(12) United States Patent
Aronov et al.

(10) Patent No.: US 8,481,538 B2
(45) Date of Patent: Jul. 9, 2013

(54) HETEROCYCLIC INHIBITORS OF C-MET AND USES THEREOF

(75) Inventors: Alexander Aronov, Newton, MA (US); Jon Come, Cambridge, MA (US); John Court, Littleton, MA (US); David Deininger, Waltham, MA (US); David Lauffer, Stow, MA (US); Pan Li, Lexington, MA (US); Kira McGinty, Schenctady, NY (US); Suganthini Nanthakumar, Newton, MA (US); Dean Stamos, Carlsbad, CA (US); Kirk Tanner, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 798 days.

(21) Appl. No.: 12/441,187

(22) PCT Filed: Sep. 18, 2007

(86) PCT No.: PCT/US2007/020222
§ 371 (c)(1),
(2), (4) Date: Feb. 12, 2010

(87) PCT Pub. No.: WO2008/036272
PCT Pub. Date: Mar. 27, 2008

(65) Prior Publication Data
US 2010/0144739 A1    Jun. 10, 2010

Related U.S. Application Data

(60) Provisional application No. 60/845,356, filed on Sep. 18, 2006.

(51) Int. Cl.
*A61K 31/5025* (2006.01)
*C07D 487/04* (2006.01)
*A61P 35/00* (2006.01)
*A61P 9/10* (2006.01)

(52) U.S. Cl.
USPC .................................. 514/248; 544/236

(58) Field of Classification Search
USPC .................................. 544/236; 514/248
See application file for complete search history.

(56) References Cited

U.S. PATENT DOCUMENTS

| 2008/0113984 A1* | 5/2008 | Cai et al. ............... 514/233.2 |
| 2011/0044943 A1* | 2/2011 | Leivers et al. ........... 424/85.4 |
| 2012/0010203 A1* | 1/2012 | Heinelt et al. ........... 514/232.5 |
| 2012/0071474 A1* | 3/2012 | Bo et al. ................ 514/233.2 |

FOREIGN PATENT DOCUMENTS

| WO | 2005/010005 | 2/2005 |
| WO | 2007/064797 | 6/2007 |

OTHER PUBLICATIONS

Eder, et al., Clin Cancer Res 2207-2214 15(7) Apr. 1, 2009.*
Tuynman, et al., Cancer Res 68: (4). Feb. 15, 2008, 1213-1220.*
Liu, et al., Clin Cancer Res 2011;17:7127-7138. Published Online1st Sep. 14, 2011.*
Milligan, et al., Clin Cancer Res 2009;15:4885-4894, published Online1st Jul. 28, 2009.*
Rob Toreki's Organometallic HyperTextBook, last updated Nov. 20, 2003, <http://www.ilpi.com/organomet/alkylidene.html>, pp. 1-3.*
Chemicool, 2012, <http://www.chemicool.com/definition/alkylidene_groups.html>, p. 1.*

* cited by examiner

*Primary Examiner* — Susanna Moore
*Assistant Examiner* — Cecilia M Jaisle
(74) *Attorney, Agent, or Firm* — Daniel A. Pearson

(57) ABSTRACT

The present invention provides compounds useful as inhibitors of c-Met tyrosine kinase. The invention also provides pharmaceutically acceptable compositions comprising the compounds of the invention and methods of using the compositions in the treatment of various proliferative disorders.

13 Claims, No Drawings

HETEROCYCLIC INHIBITORS OF C-MET AND USES THEREOF

CROSS-REFERENCE TO RELATED APPLICATIONS

This present application claims the benefit, under 35 U.S.C. §119, to U.S. Provisional Application No. 60/845,356, filed Sep. 18, 2006, and under 35 U.S.C. §371 to International Patent Application No. PCT/US2007/020222, filed Sep. 18, 2007, the entire disclosures of which are incorporated herein by reference.

BACKGROUND OF THE INVENTION

The present invention relates to compounds useful as inhibitors of c-Met.

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase. c-Met, a widely expressed heterodimeric protein comprising of a 50 kilodalton (kDa) α-subunit and a 145 kDa β-subunit, is overexpressed in a significant percentage of various types of human cancers and is often amplified during the transition between primary tumors and metastasis. c-Met is also implicated in atherosclerosis and lung fibrosis.

Accordingly, there is a great need to develop compounds useful as inhibitors of c-Met protein kinase receptor.

SUMMARY OF THE INVENTION

It has been found that compounds of this invention, and pharmaceutically acceptable compositions thereof, are effective as inhibitors of c-Met. Accordingly, the invention features compounds having the formula:

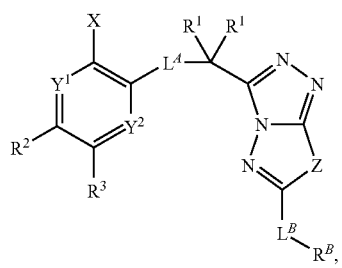

(I)

or a pharmaceutically acceptable salt or prodrug thereof, where each of $R^1$, $R^2$, $R^3$, X, $Y^1$, $Y^2$, Z, $L^A$, $L^B$, and $R^B$ is as defined herein.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds. The term "alkylidene," as used herein, represents a divalent straight chain alkyl linking group.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" means alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; —$R^°$; —$OR^°$; —$SR^°$; 1,2-methylenedioxy; 1,2-ethylenedioxy; phenyl (Ph), optionally substituted with $R^°$; —O(Ph), optionally substituted with $R^°$; —$(CH_2)_{1-2}$(Ph), optionally substituted with $R^°$; —CH=CH(Ph), optionally substituted with $R^°$; —$NO_2$; —CN; —$N(R^°)_2$; —$NR^°C(O)R^°$; —$NR^°C(S)R^°$; —$NR^°C(O)N(R^°)_2$; —$NR^°C(S)N(R^°)_2$; —$NR^°CO_2R^°$; —$NR^°NR^°C(O)R^°$; —$NR^°NR^°C(O)N(R^°)_2$; —$NR^°NR^°CO_2R^°$; —$C(O)C(O)R^°$; —$C(O)CH_2C(O)R^°$; —$CO_2R^°$; —$C(O)R^°$; —$C(S)R^°$; —$C(O)N(R^°)_2$; —$C(S)N(R^°)_2$; —$B(OR^°)_2$; —$OC(O)N(R^°)_2$; —$OC(O)R^°$; —$C(O)N(OR^°R^°$; —$C(NOR^°R^°$; —$S(O)_2R^°$; —$S(O)_3R^°$; —$SO_2N(R^°)_2$; —$S(O)R^°$; —$NR^°SO_2N(R^°)_2$; —$NR^°SO_2R^°$; —$N(OR^°R^°$; —C(=NH)—$N(R^°)_2$; —$(CH_2)_{0-2}NHC(O)R^°$; -L-$R^°$; -L-$N(R^°_2$; -L-$SR^°$; -L-$OR^°$; -L-($C_{3-10}$ cycloaliphatic), -L-($C_{6-10}$ aryl), -L-(5-10 membered heteroaryl), -L-(5-10 membered heterocyclyl), oxo, $C_{1-4}$ haloalkoxy, $C_{1-4}$ haloalkyl, -L-$NO_2$, -L-CN, -L-OH, -L-$CF_3$; or two substituents, on the same carbon or on different carbons, together with the carbon or intervening carbons to which they are bound, form a 5-7 membered saturated, unsaturated, or partially saturated ring, wherein L is a $C_{1-6}$ alkylene group in which up to three methylene units are replaced by —NH—, —NR°—, —O—, —S—, —CO$_2$—, —OC(O)—, —C(O)CO—, —C(O)—, —C(O)NH—, —C(O)NR°—, —C(=N—CN)—, —NHCO—, —NR°CO—, —NHC(O)O—, —NR°C(O)O—, —SO$_2$NH—, —SO$_2$NR°—, —NHSO$_2$—, —NR°SO$_2$—, —NHC(O)NH—, —NR°C(O)NH—, —NHC(O)NR°—, —NR°C(O)NR°—, —OC(O)NH—, —OC(O)NR°—, —NHSO$_2$NH—, —NR°SO$_2$NH—, —NHSO$_2$NR°—, —NR°SO$_2$NR°—, —SO—, or —SO$_2$—, and wherein each occurrence of R° is independently selected from hydrogen, optionally substituted $C_{1-6}$ aliphatic, an unsubstituted 5- to 6-membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Optional substituents on the aliphatic group of R° are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo$C_{1-4}$ aliphatic), or halo$C_{1-4}$ aliphatic, wherein each of the foregoing $C_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo-$C_{1-4}$ aliphatic), and halo($C_{1-4}$ aliphatic), where each of the foregoing $C_{1-4}$ aliphatic groups of R* is unsubstituted.

In some embodiments, optional substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo($C_{1-4}$ aliphatic)), or halo ($C_{1-4}$ aliphatic), wherein each of the foregoing $C_{1-4}$ aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

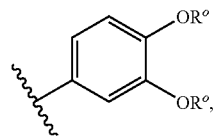

these two occurrences of R° are taken together with the oxygen atoms to which they are bound to form a fused 6-membered oxygen containing ring:

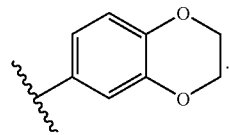 [SMILES: *c1ccc2c(c1)OCCO2]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, FIGURE a represents possible substitution in any of the positions shown in FIGURE b.

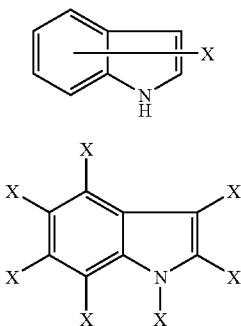

Figure a

Figure b

This also applies to multiple ring systems fused to optional ring systems (which would be represented by dotted lines). For example, in FIGURE c, X is an optional substituent both for ring A and ring B.

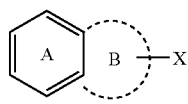

Figure c

If, however, two rings in a multiple ring system each have different substituents drawn from the center of each ring, then, unless otherwise specified, each substituent only represents substitution on the ring to which it is attached. For example, in FIGURE d, Y is an optionally substituent for ring A only, and X is an optional substituent for ring B only.

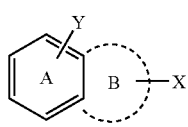

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, II, II-a, II-b, II-c, II-d, III, III-a, III-b, III-c, III-d, or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Description of Compounds of the Invention

In one aspect, the present invention features compounds having the formula:

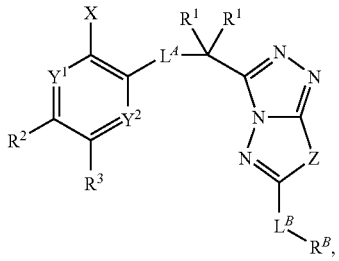

(I)

or a pharmaceutically acceptable salt or prodrug thereof, where $L^A$ is selected from —C(O)NR$^4$—, —C(S)NR$^4$—, —S(O)$_2$NR$^4$—, —NR$^4$C(O)—, —NR$^4$C(S)—, —NR$^4$S(O)$_2$—, —NR$^4$C(O)NR$^4$—, —NR$^4$C(S)NR$^4$—, or —C(R$^4$)$_2$Q-, wherein Q is —NR$^S$—, —O—, —S—, —S(O)—, or —S(O)$_2$—;

X is hydrogen, halogen, —OH, —OR$^5$, —SR$^5$, —CN, or —N(R$^5$)$_2$, or X together with C(R$^4$)$_2$ of $L^A$ forms a 5- or 6-membered heteroaromatic ring containing 1 to 2 heteroatoms selected from N, O, or S;

each of $Y^1$ or $Y^2$ is N or CH, wherein at least one of $Y^1$ or $Y^2$ must be N;

Z is —S— or —CH=CH—;

each R$^1$ is, independently, hydrogen or C$_{1-4}$ aliphatic, optionally substituted with substituents independently selected from halogen, —OH, —OR$^5$, —SR$^5$, —NO$_2$, —CN, or —N(R$^5$)$_2$, or two R$^1$ groups bonded to the same carbon form a 3-5 membered ring, optionally containing 1-2 atoms selected from N, O, or S;

R$^2$ is hydrogen, halogen, or C$_{1-4}$ aliphatic, or R$^2$ and R$^3$, together with the carbons to which they are bonded, form a 6-membered aryl or 5-6 membered heteroaryl ring, wherein either ring is optionally substituted with up to two R$^{Ar1}$;

R$^3$ is a C$_{1-8}$ aliphatic or C$_3$-C$_8$ cycloaliphatic group, optionally substituted with R; a 6 or 10 membered aryl; a 5-10 membered heteroaryl having 1-4 heteroatoms independently selected from nitrogen, oxygen, and sulfur; or a 3-10 membered heterocyclyl having 1-4 heteroatoms independently selected from nitrogen, oxygen, and sulfur; wherein each of said aryl, heteroaryl, or heterocyclyl is optionally substituted with one to five R$^{Ar1}$ or R$^3$ and R$^2$, together, form a 6-membered aryl or 5-6 membered heteroaryl ring, wherein either ring is optionally substituted with up to two R$^{Ar1}$;

each R$^4$ is, independently, hydrogen or a C$_{1-4}$ aliphatic, optionally substituted with 1-5 groups independently selected from halogen, C$_{1-4}$ aliphatic, halo(C$_{1-4}$ aliphatic), OR$^5$, O(halo(C$_{1-4}$ aliphatic)), NO$_2$, CN, CO$_2$R$^5$, C(O)N(R$^5$)$_2$, or N(R$^5$)$_2$;

$L^B$ is a covalent bond between R$^B$ and the carbon to which $L^B$ is bonded, or is a saturated or unsaturated C$_{1-4}$ alkylidene chain which is optionally substituted with 1-5 groups independently selected from halogen, C$_{1-4}$ aliphatic, halo(C$_{1-4}$ aliphatic), OR$^5$, O(halo(C$_{1-4}$ aliphatic)), NO$_2$, CN, CO$_2$R$^5$, C(O)N(R$^5$)$_2$, or N(R$^5$)$_2$, wherein up to two saturated carbons of said alkylidene chain are replaced by —C(O)—, —C(O)N(R$^5$)—, —C(O)N(R$^5$)N(R$^5$)—, —CO$_2$—, —N(R$^5$)—, —N(R$^5$)C(O)—, —N(R$^5$)CO$_2$—, —N(R$^5$)S(O)$_2$—, —N(R$^5$)C(O)N(R$^5$)—, —N(R$^5$)N(R$^5$)—, —O—, —OC(O)—, —OC(O)N(R$^5$)—, —S—, —SO—, —S(O)$_2$—, or —S(O)$_2$N(R$^5$)—;

R$^B$ is hydrogen, a C$_{1-8}$ aliphatic or C$_3$-C$_8$ cycloaliphatic group, optionally substituted with R; a 6 or 10 membered aryl ring; a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with one to five R$^{Ar2}$;

R is halogen, —R$^6$, —OR$^6$, —SR$^6$, —OC(O)(C$_{1-8}$ aliphatic), Ph optionally substituted with R$^6$, —O(Ph) optionally substituted with R$^6$, —CH$_2$(Ph) optionally substituted with R$^6$, —CH$_2$CH$_2$(Ph) optionally substituted with R$^6$, —NO$_2$, —CN, —N(R$^6$)$_2$, —NR$^6$C(O)R$^6$, —NR$^6$C(O)N(R$^6$)$_2$, —NR$^6$CO$_2$R$^6$, —NR$^6$NR$^6$C(O)R$^6$, —NR$^6$NR$^6$C(O)N(R$^6$)$_2$, —NR$^6$NR$^6$CO$_2$R$^6$, —C(O)C(O)R$^6$, —C(O)CH$_2$C(O)R$^6$, —CO$_2$R$^6$, —C(O)R$^6$, —C(O)N(R$^6$)$_2$, —OC(O)N(R$^6$)$_2$, —S(O)$_2$R$^6$, —SO$_2$N(R$^6$)$_2$, —S(O)R$^6$, —NR$^6$SO$_2$N(R$^6$)$_2$, —NR$^6$SO$_2$R$^6$, —C(=S)N(R$^6$)$_2$, —C(=NH)—N(R$^6$)$_2$, or —(CH$_2$)$_y$NHC(O)R$^6$, wherein y is 1 to 4; or two R together on the same carbon atom are =O, =S, =NNHR$^7$, =NN(R$^7$)$_2$, =NNHC(O)R$^7$, =NNHCO$_2$(C$_{1-8}$ aliphatic), =NNHSO$_2$(C$_{1-8}$ aliphatic), or =NR$^7$;

each R$^{Ar1}$ or R$^{Ar2}$ is, independently, selected from halogen, —R$^6$, —OR$^6$, —SR$^6$, Ph optionally substituted with one to five R$^6$, —O(Ph) optionally substituted with one or more R$^6$, —(CH$_2$)$_y$(Ph) optionally substituted with one to five R$^6$, —NO$_2$, —CN, —N(R$^6$)$_2$, —NR$^6$C(O)R$^6$, —NR$^6$C(O)N(R$^6$)$_2$, —NR$^6$CO$_2$R$^6$, —NR$^6$NR$^6$C(O)R$^6$, —NR$^6$NR$^6$C(O)N(R$^6$)$_2$, —NR$^6$NR$^6$CO$_2$R$^6$, —C(O)CH$_2$C(O)R$^6$, —CO$_2$R$^6$, —C(O)R$^6$, —C(O)N(R$^6$)$_2$, —OC(O)N(R$^6$)$_2$, —S(O)$_2$R$^6$, —SO$_2$N(R$^6$)$_2$, —S(O)R$^6$, —NR$^6$SO$_2$N(R$^6$)$_2$, —NR$^6$SO$_2$R$^6$, —C(S)N(R$^6$)$_2$, —C(NH)N(R$^6$)$_2$, and —(CH$_2$)$_y$NHC(O)R$^6$, wherein y is 1 to 4; or two adjacent R$^{Ar1}$ or R$^{Ar2}$ together are 1,2-methylenedioxy or 1,2-ethylenedioxy;

each R$^5$ is, independently, hydrogen or C$_{1-4}$ aliphatic;

each R$^7$ is, independently, hydrogen or an optionally substituted C$_{1-8}$ aliphatic, wherein each substituent of said optionally substituted aliphatic of R$^7$ is, independently, —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic) —NO$_2$, —CN, —CO$_2$H, —CO$_2$(C$_{1-4}$ aliphatic), —C(O)NH$_2$, —C(O)NH(C$_{1-4}$ aliphatic), —C(O)N(C$_{1-4}$ aliphatic)$_2$, —O(halo(C$_{1-4}$ aliphatic)), or halo(C$_{1-4}$ aliphatic); or two R$^7$ on the same nitrogen are taken together with the nitrogen to form a 5-8 membered heterocyclyl or heteroaryl ring having 1-3 heteroatoms independently selected from nitrogen, oxygen, and sulfur; and each R$^6$ is, independently, hydrogen, optionally substituted C$_{1-6}$ aliphatic, an unsubstituted 5-6 membered heteroaryl or heterocyclic ring, -Ph, or —O(Ph), wherein each substituent of said optionally substituted aliphatic of R$^6$ is, independently, —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —C(O)NH$_2$, —C(O)NH(C$_{1-4}$ aliphatic), —C(O)N(C$_{1-4}$ aliphatic)$_2$, —O(halo(C$_{1-4}$ aliphatic)), or halo(C$_{1-4}$ aliphatic); or two R$^6$ on the same nitrogen are taken together with the nitrogen to form a 5-8 membered heterocyclyl or heteroaryl ring having 1-3 heteroatoms independently selected from nitrogen, oxygen, and sulfur.

In one embodiment, X is hydrogen or —N(R$^5$)$_2$.
In another embodiment, each of $Y^1$ and $Y^2$ is N.
In yet another embodiment, $Y^1$ is N and $Y^2$ is CH.

In other embodiments, compounds of the invention have formula:

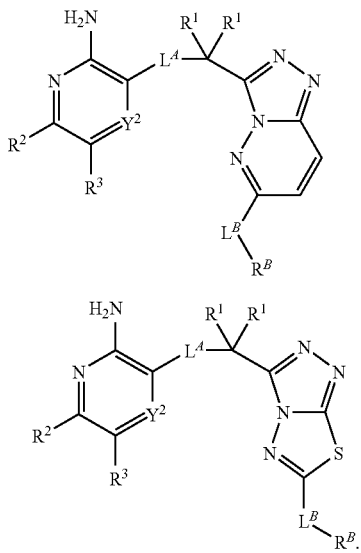

(II)

(III)

In still other embodiments, compounds of the invention have formula:

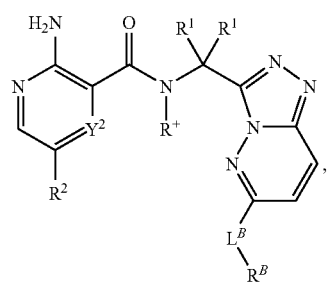

(IIa)

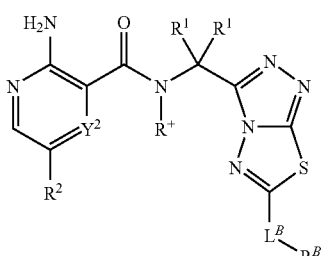

(IIIa)

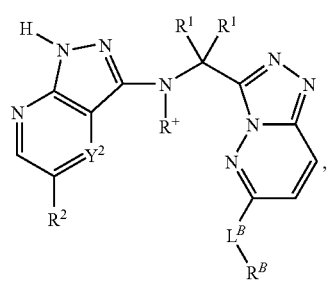

(IIb)

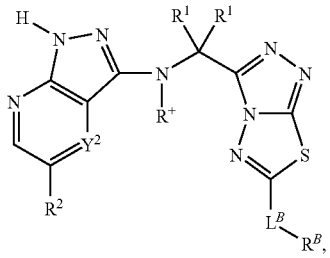

(IIIb)

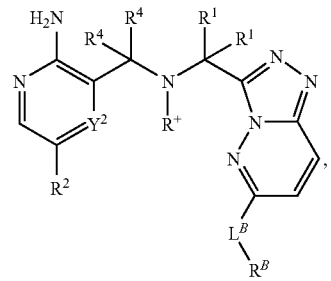

(IIc)

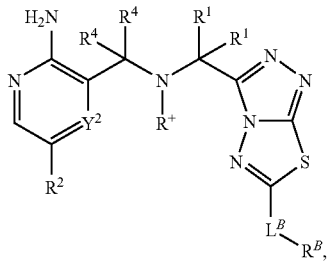

(IIIc)

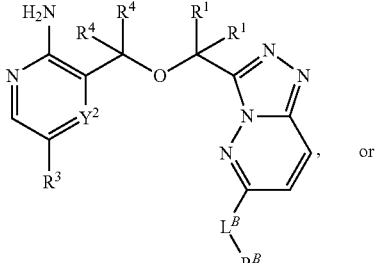

(IId)

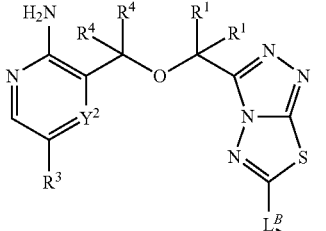

(IIId)

In one embodiment, $L^B$ is a covalent bond, —CH$_2$—, or —N(R$^5$)— in any of the compounds of formula I, II, II-a, II-b, II-c, II-d, III, III-a, III-b, Iii-c, or III-d. In a further embodiment, $L^B$ is —N(R$^5$)—. In a still further embodiment, $L^B$ is —NH—.

In one embodiment for any compounds of formula I, II, II-a, II-b, II-c, II-d, III, III-a, III-b, Iii-a, or III-d, $R^B$ is a C$_{1-8}$ aliphatic or C$_3$-C$_8$ cycloaliphatic group, optionally substituted with R; a 6 or 10 membered aryl ring; a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with one to five $R^{Ar2}$. In another embodiment, $R^B$ is an optionally substituted phenyl or 5-6 membered heteroaryl ring. In another embodiment, $R^B$ is an optionally substituted heteroaryl ring selected from furan, thiophene, pyrrole, pyrazole, imidazole, oxazole, or thiazole. In a further embodiment, $R^B$ is a phenyl ring substituted in the 3-position.

In yet another embodiment, $R^3$ is an optionally substituted phenyl or 5-6 membered heteroaryl ring in any compounds of formula I, II, II-a, II-b, II-c, II-d, III, III-a, III-b, III-a, or III-d, such as, for example, a heteroaryl ring selected from furan, thiophene, pyrrole, pyrazole, imidazole, oxazole, or thiazole.

In another aspect, the invention features a compound selected from the group of compounds listed in Table 1.

TABLE 1

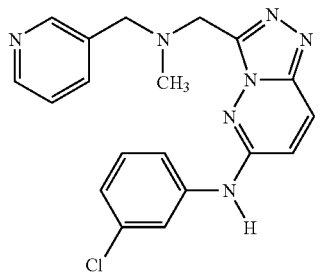

1

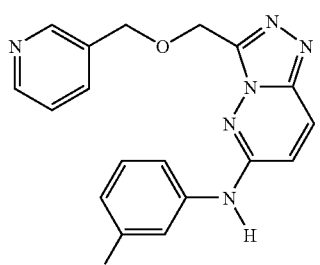

2

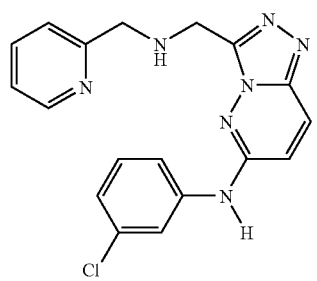

3

TABLE 1-continued

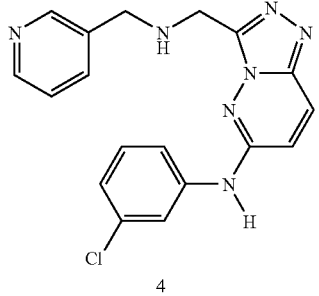 [SMILES: Clc1cccc(Nc2ccc3nnc(CNCc4cccnc4)n3n2)c1]

4

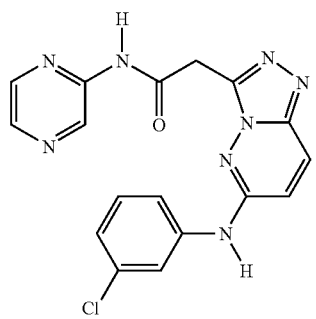

5

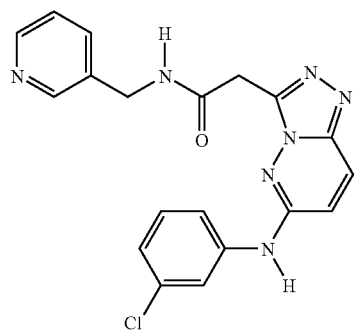

6

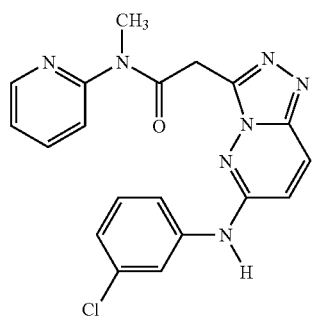

7

TABLE 1-continued
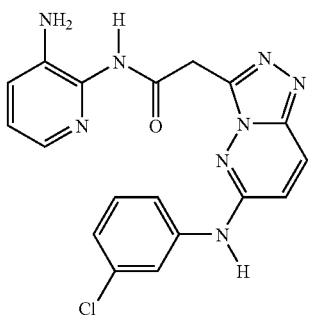
8
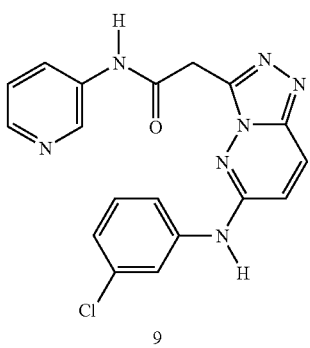 [SMILES: O=C(Cc1nnc2ccc(Nc3cccc(Cl)c3)nn12)Nc1cccnc1]
9
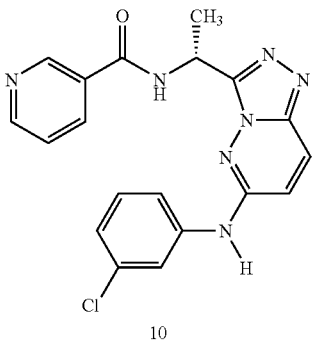 [SMILES: C[C@@H](NC(=O)c1cccnc1)c1nnc2ccc(Nc3cccc(Cl)c3)nn12]
10
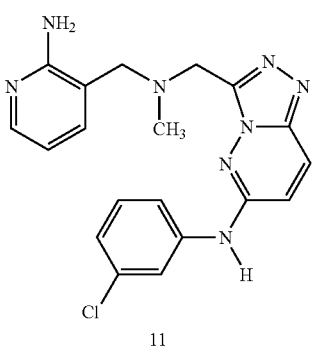 [SMILES: CN(Cc1cccnc1N)Cc1nnc2ccc(Nc3cccc(Cl)c3)nn12]
11
TABLE 1-continued
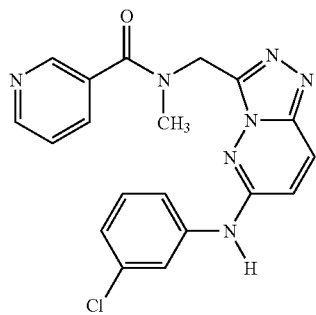
12
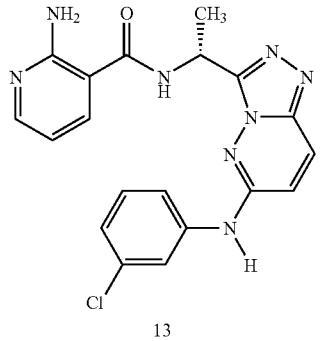 [SMILES: C[C@@H](NC(=O)c1nccnc1N)c1nnc2ccc(Nc3cccc(Cl)c3)nn12]
13
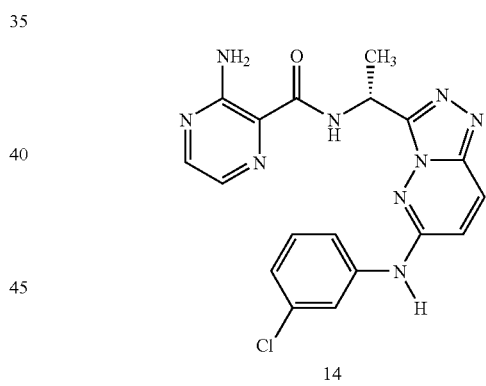
14
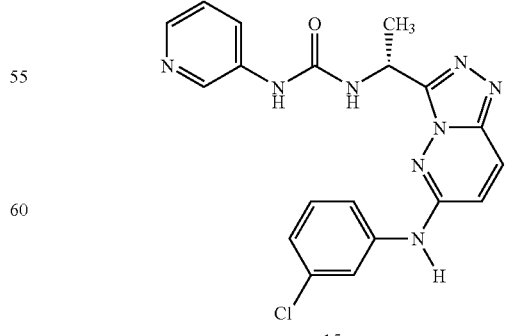
15

TABLE 1-continued
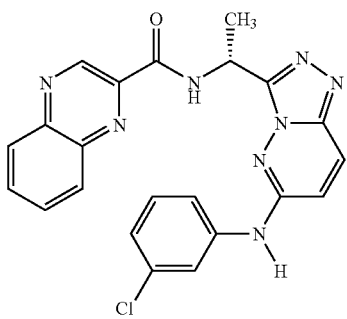
16
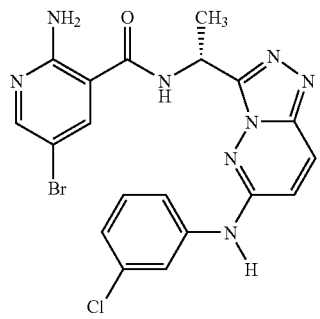
17
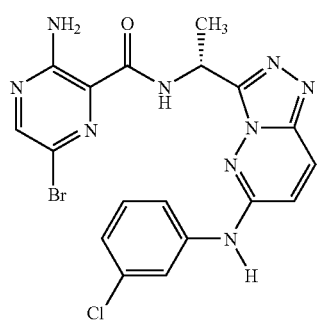
18
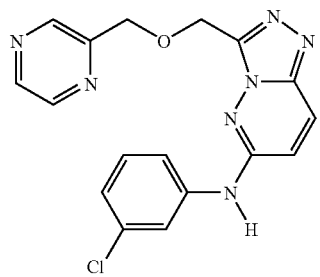
19
TABLE 1-continued
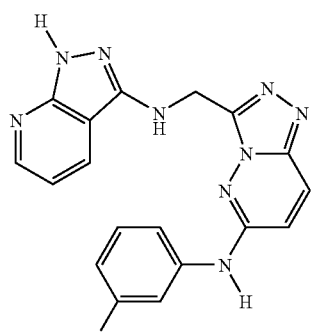
20
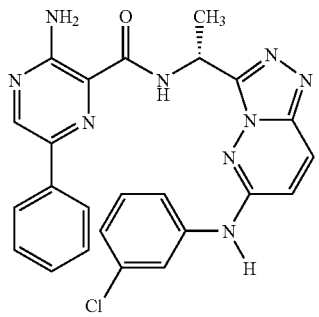
21
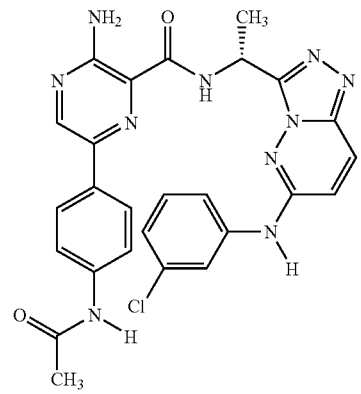
22
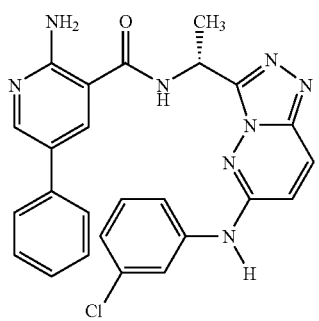
23

TABLE 1-continued
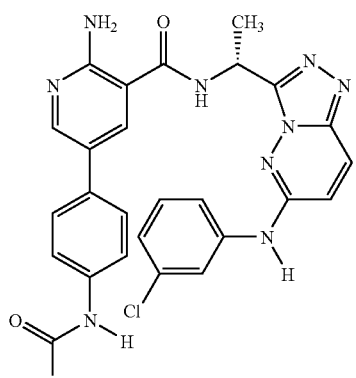
24
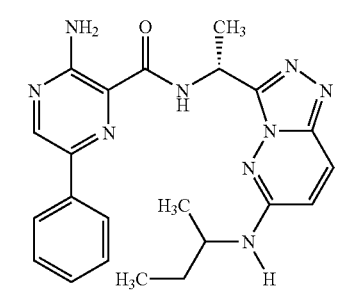
25
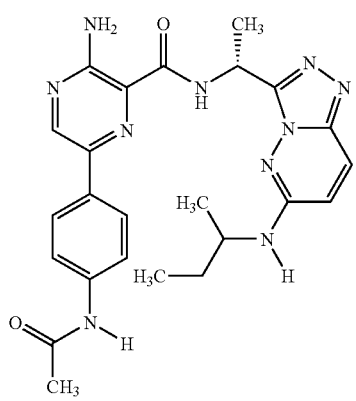
26
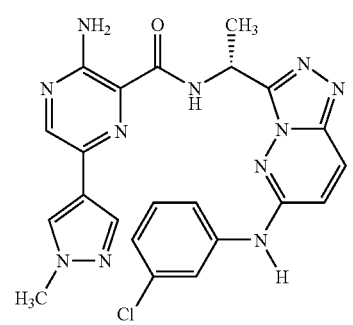
27
TABLE 1-continued
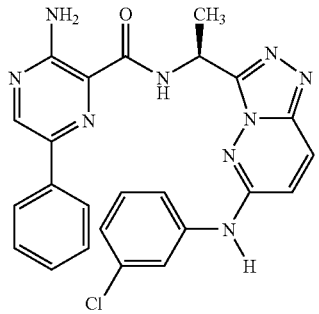
28
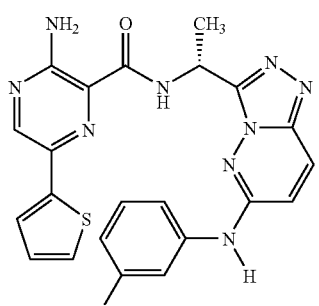
29
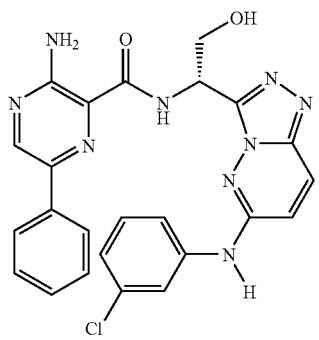
30
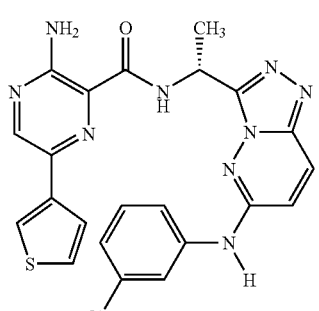
31

TABLE 1-continued
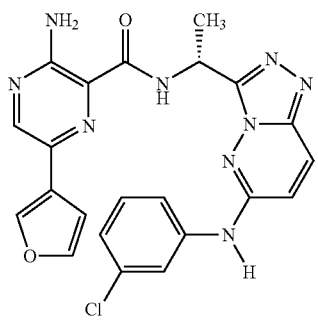
32
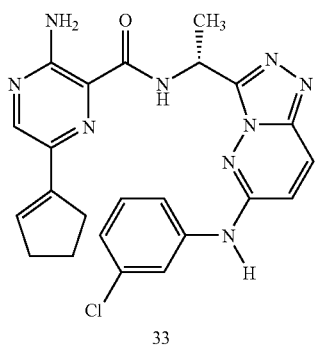 [SMILES: C[C@@H](NC(=O)c1nc(C2=CCCC2)cnc1N)c1nnc2ccc(Nc3cccc(Cl)c3)nn12]
33
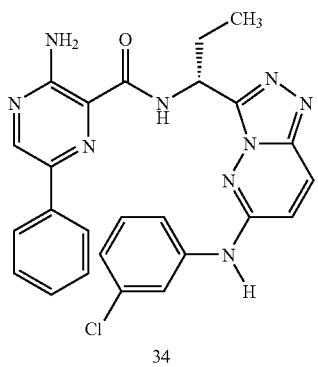 [SMILES: CC[C@@H](NC(=O)c1nc(-c2ccccc2)cnc1N)c1nnc2ccc(Nc3cccc(Cl)c3)nn12]
34
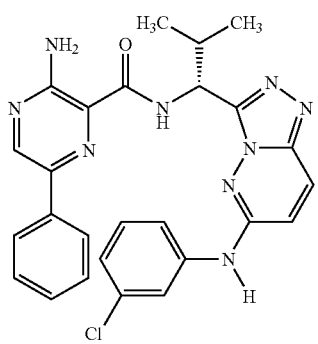
35
TABLE 1-continued
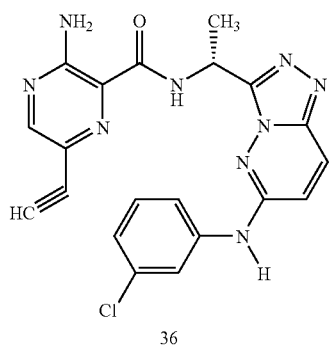 [SMILES: C#Cc1cnc(N)c(C(=O)N[C@H](C)c2nnc3ccc(Nc4cccc(Cl)c4)nn23)n1]
36
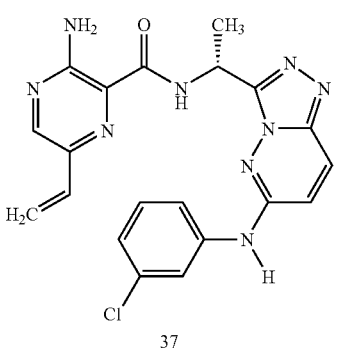 [SMILES: C=Cc1cnc(N)c(C(=O)N[C@H](C)c2nnc3ccc(Nc4cccc(Cl)c4)nn23)n1]
37
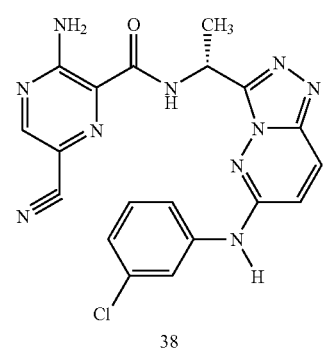 [SMILES: C[C@@H](NC(=O)c1nc(C#N)cnc1N)c1nnc2ccc(Nc3cccc(Cl)c3)nn12]
38
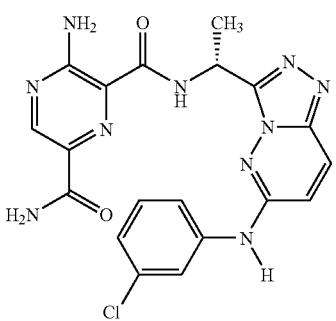
39

TABLE 1-continued
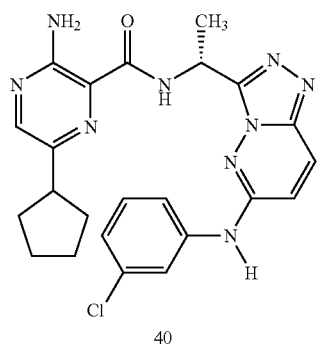 [SMILES: C[C@@H](NC(=O)c1nc(C2CCCC2)cnc1N)c1nnc2ccc(Nc3cccc(Cl)c3)nn12]
40
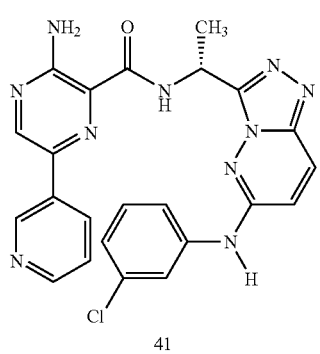
41
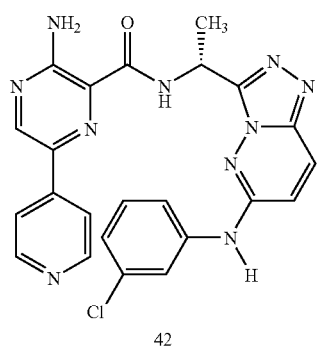 [SMILES: C[C@@H](NC(=O)c1nc(-c2ccncc2)cnc1N)c1nnc2ccc(Nc3cccc(Cl)c3)nn12]
42
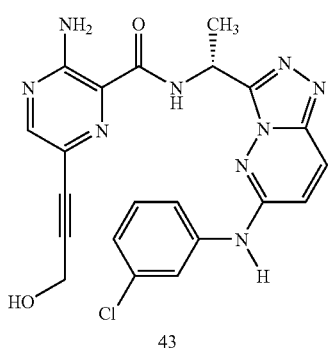 [SMILES: C[C@@H](NC(=O)c1nc(C#CCO)cnc1N)c1nnc2ccc(Nc3cccc(Cl)c3)nn12]
43
TABLE 1-continued
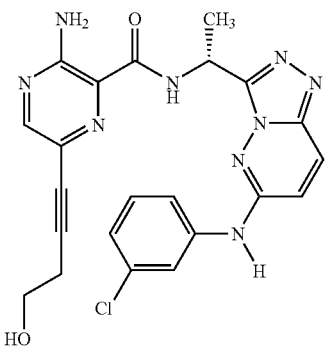
44
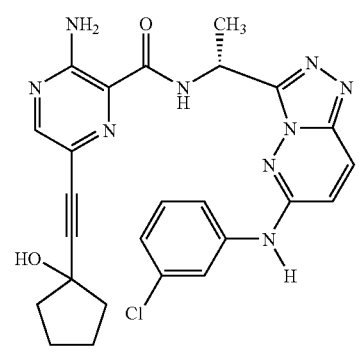
45
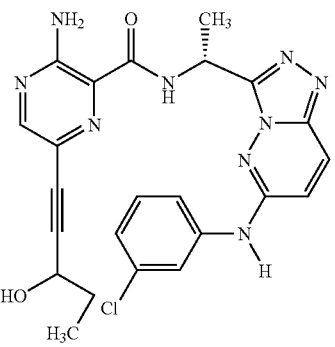
46
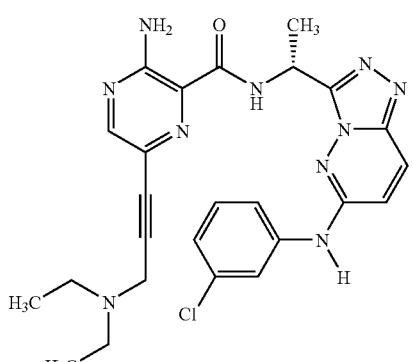
47

TABLE 1-continued
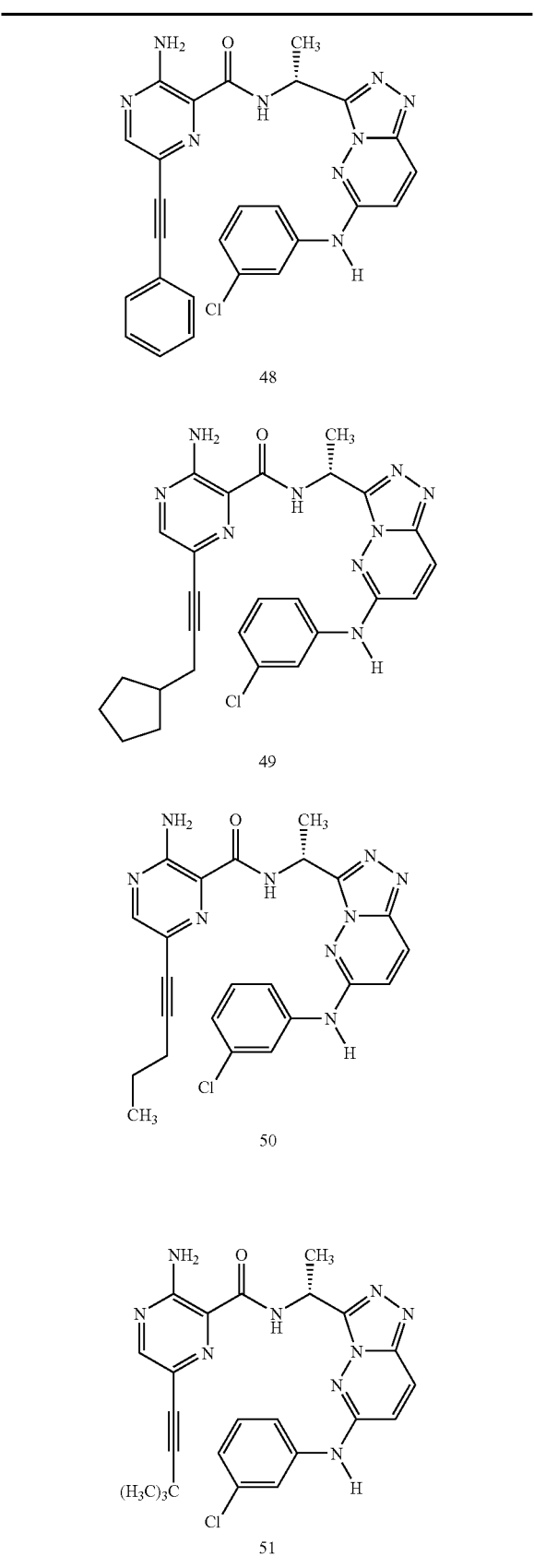
48
49
50
51
TABLE 1-continued
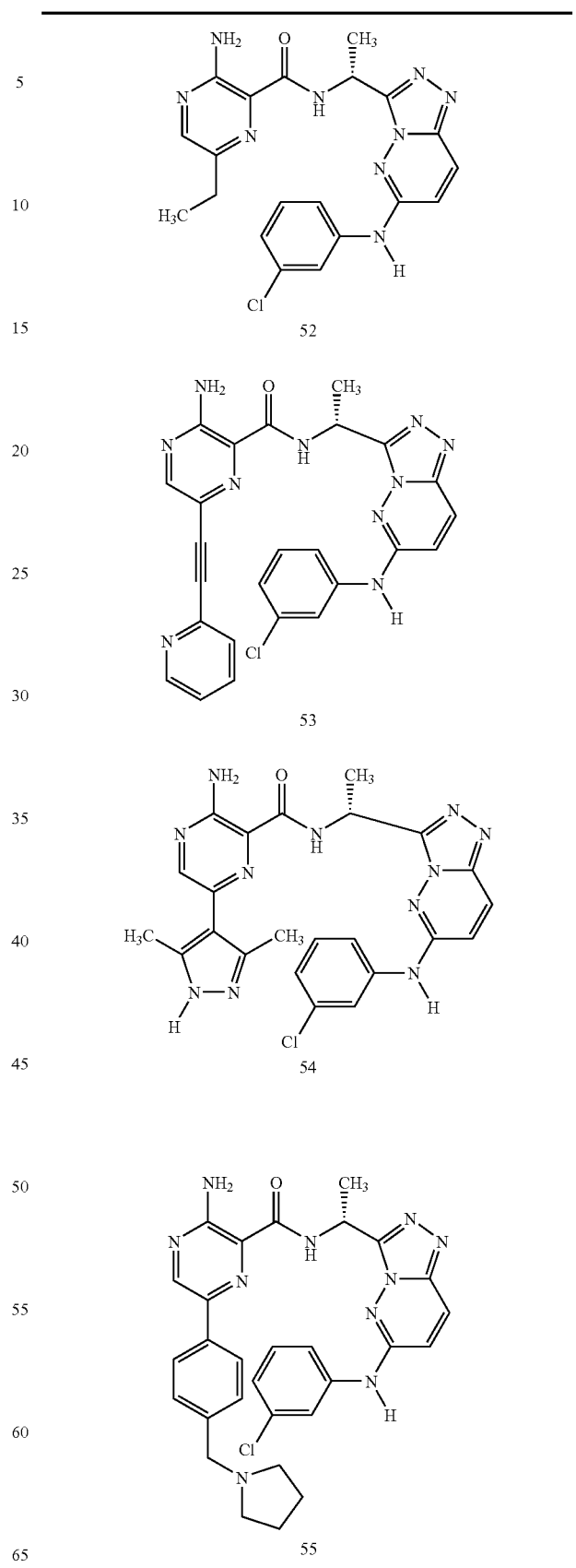
52
53
54
55

TABLE 1-continued
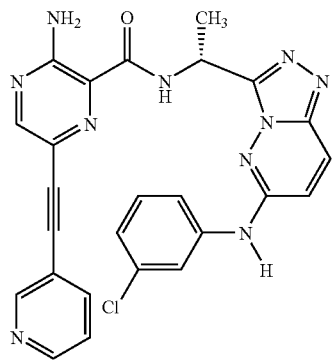
56
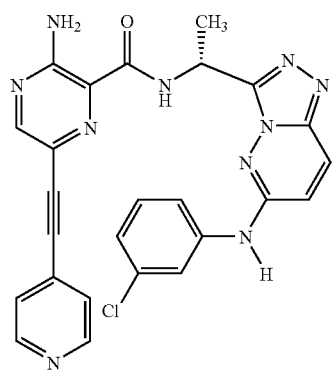
57
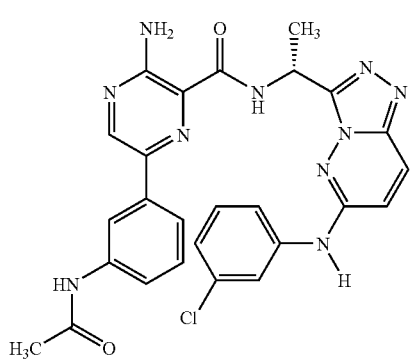
58
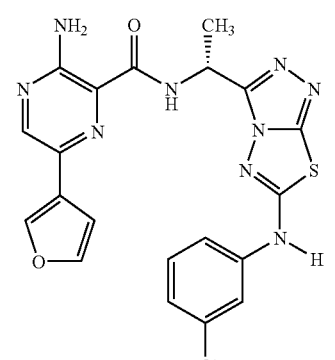
59
TABLE 1-continued
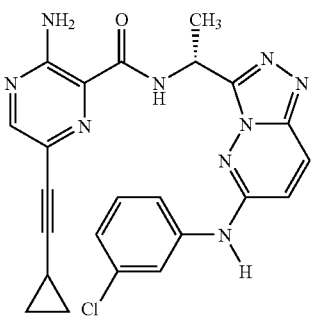
60
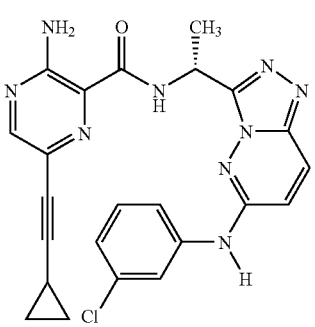
61
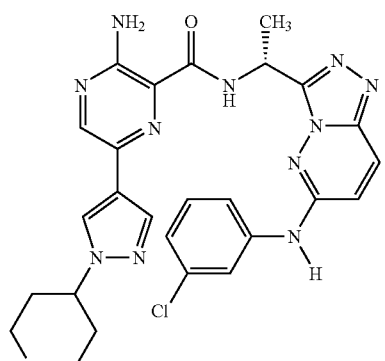
62
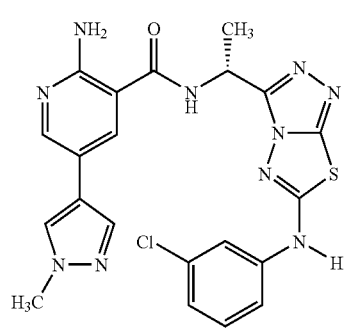
63

TABLE 1-continued
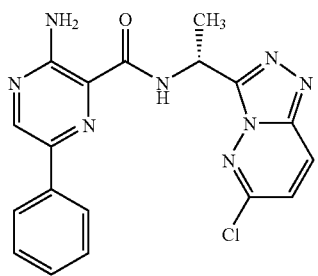
64
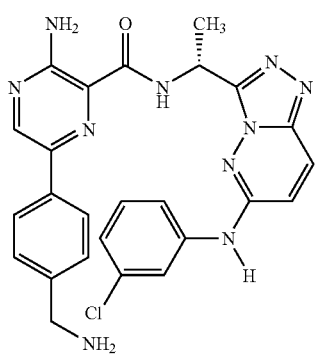
65
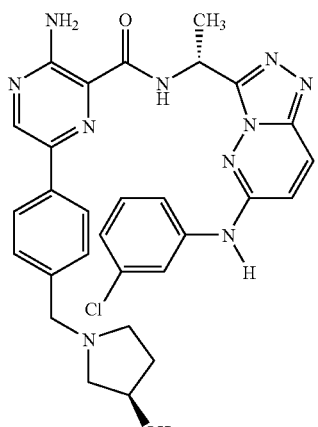
66
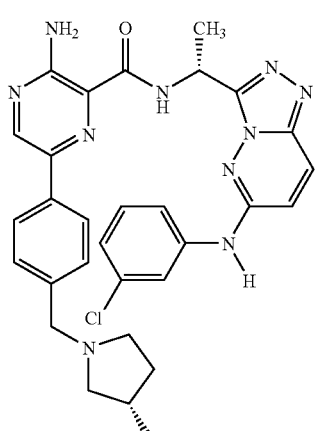 [SMILES: C[C@@H](NC(=O)c1nc(-c2ccc(CN3CCCC3)cc2)cnc1N)c1nnc2ccc(Nc3cccc(Cl)c3)nn12]
67
TABLE 1-continued
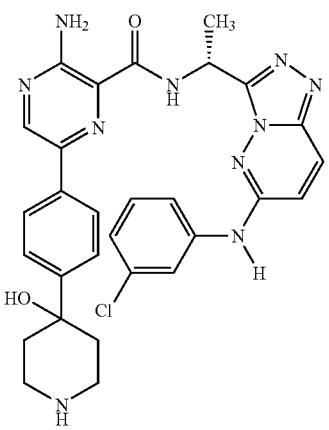
68
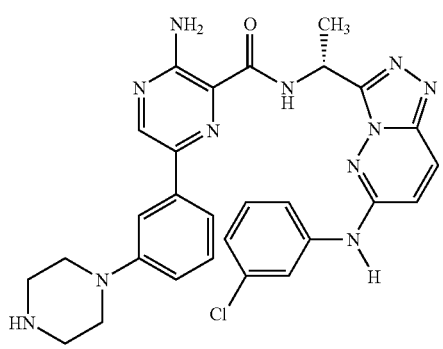
69
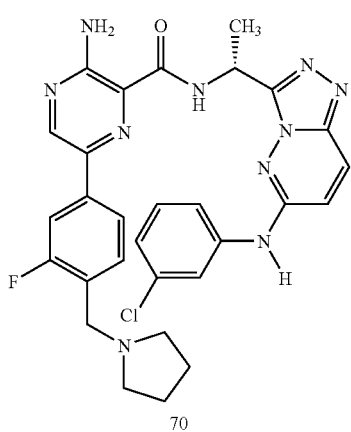 [SMILES: C[C@@H](NC(=O)c1nc(-c2ccc(CN3CCCC3)c(F)c2)cnc1N)c1nnc2ccc(Nc3cccc(Cl)c3)nn12]
70

TABLE 1-continued
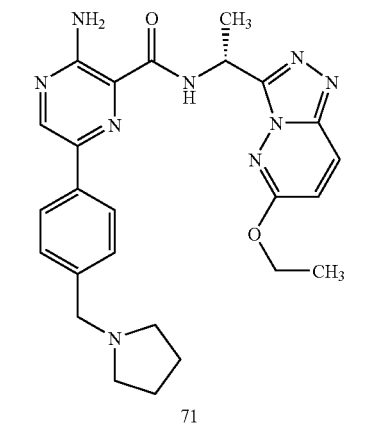 [SMILES: CCOc1ccc2nnc([C@@H](C)NC(=O)c3nc(-c4ccc(CN5CCCC5)cc4)cnc3N)n2n1]
71
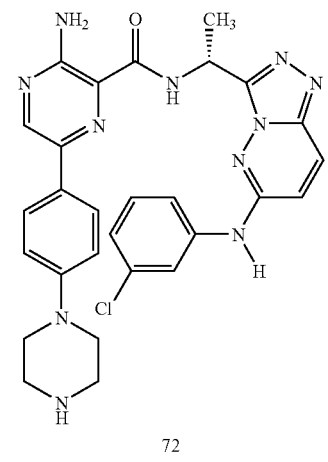 [SMILES: C[C@@H](NC(=O)c1nc(-c2ccc(N3CCNCC3)cc2)cnc1N)c1nnc2ccc(Nc3cccc(Cl)c3)nn12]
72
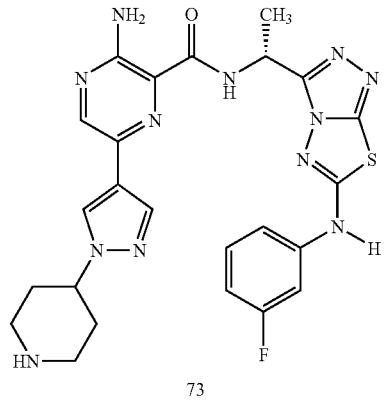 [SMILES: C[C@@H](NC(=O)c1nc(-c2cnn(C3CCNCC3)c2)cnc1N)c1nnc2sc(Nc3cccc(F)c3)nn12]
73
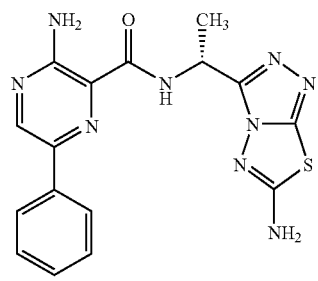
74
TABLE 1-continued
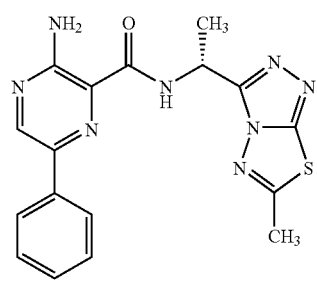
75
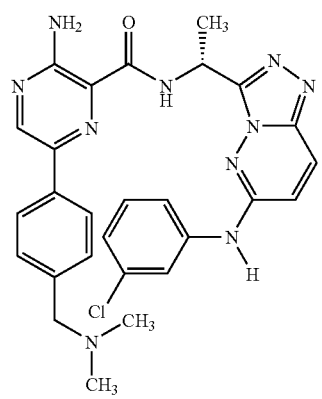
76
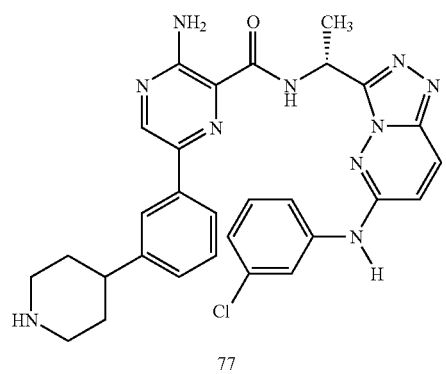 [SMILES: C[C@@H](NC(=O)c1nc(-c2cccc(C3CCNCC3)c2)cnc1N)c1nnc2ccc(Nc3cccc(Cl)c3)nn12]
77
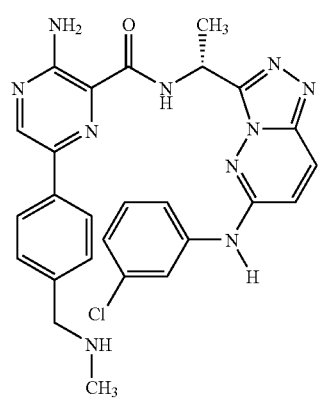
78

TABLE 1-continued

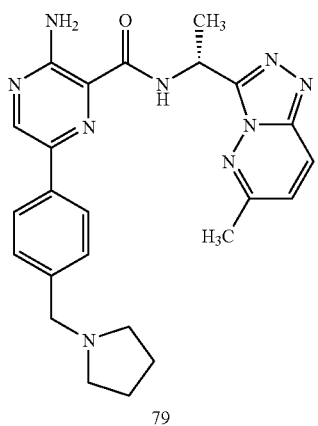 [SMILES: Cc1ccc2nnc([C@@H](C)NC(=O)c3nc(-c4ccc(CN5CCCC5)cc4)cnc3N)n2n1]

79

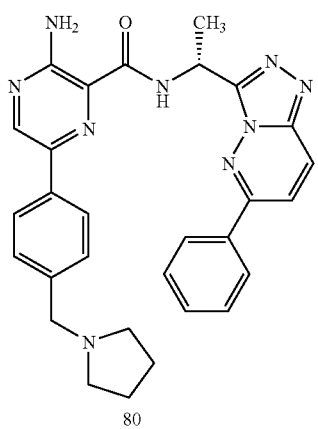 [SMILES: C[C@@H](NC(=O)c1nc(-c2ccc(CN3CCCC3)cc2)cnc1N)c1nnc2ccc(-c3ccccc3)nn12]

80

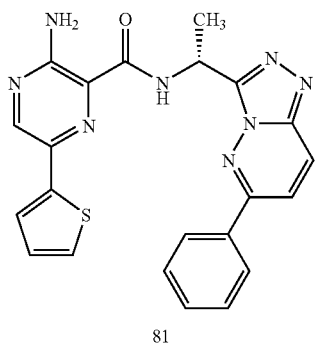 [SMILES: C[C@@H](NC(=O)c1nc(-c2cccs2)cnc1N)c1nnc2ccc(-c3ccccc3)nn12]

81

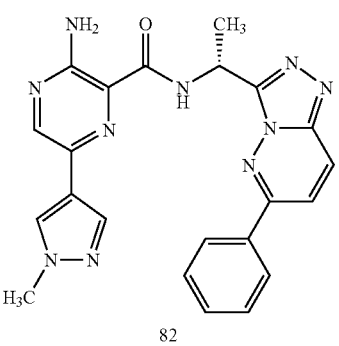 [SMILES: C[C@@H](NC(=O)c1nc(-c2cnn(C)c2)cnc1N)c1nnc2ccc(-c3ccccc3)nn12]

82

TABLE 1-continued

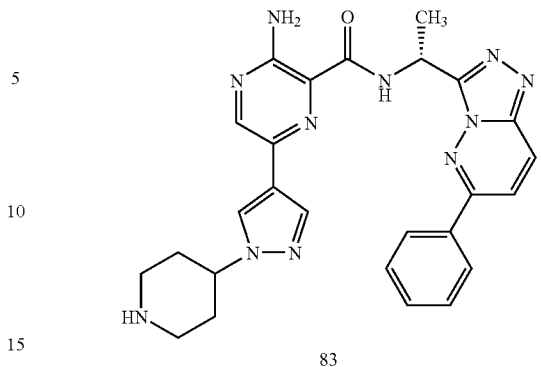

83

Compositions, Formulations, and Administration of Compounds of the Invention

According to another aspect, the invention features pharmaceutical compositions that include a compound of formula I, II-a, III-a, II-b, III-b, II-c, III-c, II-d, III-d, or a compound listed in Table 1, and a pharmaceutically acceptable carrier, adjuvant, or vehicle. The amount of compound in the compositions of the invention is such that is effective to detectably inhibit a protein kinase, particularly c-Met in a biological sample or in a patient.

Preferably a composition of the present invention is formulated for administration to a patient in need of such composition. Most preferably, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof. As used herein, the term "inhibitory active metabolite or residue thereof" means that a metabolite or residue thereof is also an inhibitor of c-Met.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

A compound or composition of the invention can be used as a monotherapy to treat or lessen the severity of a proliferative disease, condition, or disorder in a patient by administering to the patient a compound or a composition of the invention in an effective amount. Such diseases, conditions, or disorders include cancer, particularly metastatic cancer, atherosclerosis, and lung fibrosis.

As used herein, the term "c-Met" is synonymous with "cMet", "MET", "Met," "hepatocyte growth factor receptor," or other designations known to one skilled in the art.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include adrenocortical cancer; bladder cancer; bone cancer; brain cancer; breast cancer; cancer of the peritoneum; cervical cancer; colon cancer; colorectal cancer; endometrial or uterine carcinoma; esophageal cancer; eye cancer; gallbladder cancer; gastrointestinal cancer; glioblastoma; various types of head and neck cancer; hepatic carcinoma; hepatocellular cancer; kidney carcinoma; laryngeal cancer; liver cancer; lung cancer, such as, for example, adenocarcinoma of the lung, small-cell lung cancer, squamous carcinoma of the lung, non-small cell lung cancer; melanoma and nonmelanoma skin cancer; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia; ovarian cancer; pancreatic cancer; prostate cancer, including benign prostatic hyperplasia; rectal cancer; salivary gland carcinoma; squamous cell cancer; testicular cancer; thyroid cancer; and vulval cancer.

The treatment method that includes administering a c-Met inhibitor of the invention can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months. Non-limiting examples of chemotherapeutic agents or other anti-proliferative agents that may be combined with the compounds of this invention include adriamycin, gemcitabine, cyclophosphamide, dexamethasone, etoposide, fluorouracil, Gleevec™, interferons, platinum derivatives, such as carboplatin, topotecan, taxol, vinblastine, and vincristine.

The invention also features a method of inhibiting the growth of a cell that expresses c-Met or hepatocyte growth factor, or both, that includes contacting the cell with a compound or composition of the invention, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention provides a method of inhibiting c-Met kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly c-Met kinase activity, in a biological sample is useful for a variety of purposes known to one of skill in the art. Examples of such purposes include, but are not limited to, blood transfusion, organ-transplantation, biological specimen storage, and biological assays.

The invention also provides a method of inhibiting c-Met kinase activity in a patient, comprising administering to the patient a compound or composition of the invention. In an embodiment, the invention comprises a method of treating or lessening the severity of a c-Met-mediated condition or disease in a patient. The term "c-Met-mediated disease" or "c-MET-mediated condition", as used herein, means any disease state or other deleterious condition in which c-Met is known to play a role. The terms "c-Met-mediated disease" or "c-Met-mediated condition" also mean those diseases or conditions that are alleviated by treatment with a c-Met inhibitor. Such conditions include, without limitation, cancers, such as, for example, colon cancer, gastric adenocarcinoma, bladder cancer, breast cancer, kidney cancer, liver cancer, lung cancer, thyroid cancer, cancer of the head and neck, prostate cancer, pancreatic cancer, cancer of the CNS, gliobastoma, or a myeloproliferative disorder, or other proliferative diseases, such as, for example, atherosclerosis and lung fibrosis.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound of this invention are another embodiment of the present invention. The compounds may also be coated on implantable medical devices, such as beads, or co-formulated with a polymer or other molecule, to provide a "drug depot," thus permitting the drug to be released over a longer time period than administration of an aqueous solution of the drug.

Preparation of Compounds of the Invention

The following definitions describe terms and abbreviations used herein:

| | |
|---|---|
| Ala | alanine |
| ATP | adenosine triphosphate |
| Boc | t-butoxylcarbonyl |
| BSA | bovine serum albumin |
| DIEA | diisopropylethylamine |
| DMF | dimethylformamide |
| DMSO | methylsulfoxide |
| DTT | dithiothreitol |
| EDCI | 1-ethyl-3-(3'-dimethylaminopropyl) carbodiimide hydrochloride |
| ESMS | electrospray mass spectrometry |
| Et$_2$O | ethyl ether |
| EtOAc | ethyl acetate |
| EtOH | ethyl alcohol |
| HBTU | O-(benzotriazol-1-yl)-1,1,3,3-tetramethyluronium hexafluorophosphate |
| HEPES | 4-(2-hydroxyethyl)-1-piperazineethanesulfonic acid |
| HOBt | hydroxy benzotriazole hydrate |
| HPLC | high performance liquid chromatography |
| LC-MS | liquid chromatography-mass spectrometry |
| Me | methyl |
| MeOH | methanol |
| NMP | N-methylpyrrolidine |
| Ph | phenyl |
| tBu | tertiary butyl |
| TCA | trichloroacetic acid |
| THF | tetrahydrofuran |
| TEA | triethylamine |
| TFA | trifluoacetic acid |

As used herein, the term "R$_t$(min)" refers to the HPLC retention time, in minutes, associated with the compound. Unless otherwise indicated, the HPLC method utilized to obtain the reported retention time is as follows: column: Zorbax SB C18 column, 3.0×150 mm; gradient: 10-90% acetonitrile/water (0.1% TFA), 5 minutes; flow rate: 1.0 mL/minute; and detection: 254 & 214 nm.

Purifications by reversed-phase HPLC were conducted on a Waters 20×100 mm YMC-Pack Pro C18 column using a linear water/acetonitrile (0.1% TFA) gradient at a flow rate of 28 mL/minute. Beginning and final composition of the gradient varied for each compound between 10-40 and 50-90% acetonitrile, respectively.

General Synthetic Procedures

In general, the compounds of this invention may be prepared by methods described herein or known to those skilled in the art for the preparation of analogous compounds. The following non-limiting schemes and examples are presented to further exemplify the invention. Physiochemical characterization of selected compounds of the invention is provided in Table 2.

I. Preparation of Triazolopyridazines

As shown in Scheme 1, a compound of formula IV, containing leaving groups LG and LG' (e.g., halogen, phosphonate, tosylate, or triflate), which can be the same or different, is reacted with up to a stoichiometric amount of hydrazine in a suitable solvent, such as, for example, isopropanol under microwave irradiation at an elevated temperature to produce a compound of formula V. Typically, the reaction temperature is above 60° C. Subsequent reaction of the compound of formula V with an imidate ester of formula VI produces a compound of formula VIII, where $R^1$ is as described herein and $R^A$ is a suitably protected functional group that can later be transformed into a nucleophilic group or a group suitable for reaction with a nucleophilic group. Typically, this reaction is performed in polar solvent at an elevated temperature, such as, for example, refluxing methanol or ethanol. In one variation, a carboxylic acid of formula VII, or ester thereof, can substitute for the imidate ester and the reaction performed neat with heating. In another variation, the carboxylic acid substituting for the imidate ester can be reacted with the hydrazine moiety using a conventional amide bond-forming reagent known to a person skilled in the art, such as, for example, 1-benzotriazol-1-yloxy-bis(pyrrolidino)uronium hexafluorophosphate (BBC), O-(7-azabenzotriazol-1-yl)-1,1,3,3-tetramethyluronium hexafluorophosphate (HATU), O-(7-azabenzotriazol-1-yl)-1,1,3,3-bis(tetramethylene)uronium hexafluorophosphate (HAPyU), O-(benzotriazol-1-yl)-1,1,3,3-tetramethyluronium hexafluorophosphate (HBTU), 1,3-diisopropylcarbodiimide (DIC), 1-ethyl-3-(3'-dimethylaminopropyl)carbodiimide hydrochloride (EDCI), O-(7-azabenzotriazol-1-yl)-tris(dimethylamino)phosphonium hexafluorophosphate (AOP), 1-benzotriazolyoxytris(dimethylamino)phosphonium hexafluorophosphate (BOP), 7-azobenzotriazolyoxytris(pyrrolidino)phosphonium hexafluorophosphate (PyABOP), and 1-benzotriazolyoxytris(pyrrolidino)phosphonium hexafluorophosphate (PyBOP). After the compound of formula VIII is prepared, it can then be reacted with a compound of formula IX, wherein $L^B$ and $R^B$ are as described elsewhere herein, in a catalyst-mediated cross coupling reaction to form a compound of formula II-A. The catalyst can be, for example, a palladium catalyst/ligand system (such as, for example, Pd(PPh$_3$)$_4$, Pd(PtBu$_3$)$_4$, Pd[P(Me)(tBu$_3$)]$_4$, PdCl$_2$(PPh$_3$)$_2$, PdCl$_2$(dppf)$_2$, Pd$_2$(dba)$_3$BINAP, or Pd$_2$(dba)$_3$P(o-tol)$_3$ (see Fu and Littke, *Angew. Chem. Int. Ed.* 41:4176-4211, 2002; Nicolaou et al., *Angew. Chem. Int. Ed.* 44:4442-4489, 2005; or Hassen et al., *Chemical Reviews* 102(5):1359-1469, 2002). The reaction is usually performed in the presence of a base. The M group of the compound of formula VI can be, for example, —B(OAlkyl)$_2$ or —B(OH)$_2$ (Suzuki reaction), —Mg—Hal (Kumada reaction), —Zn—Hal (Negishi reaction), —Sn(Alkyl)$_3$ (Stille reaction), —Si(Alkyl)$_3$ (Hiyama reaction), —Cu—Hal, —ZrCp$_2$Cl, or —AlMe$_2$.

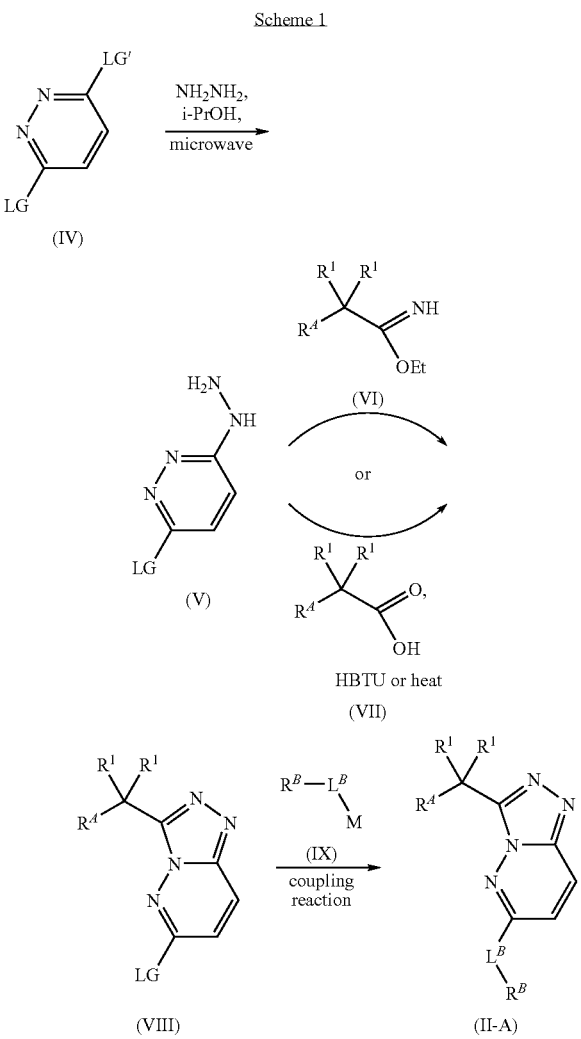

Scheme 1

If so desired, the order of the functionalization of pyridazine ring may be changed such that the cross-coupling reaction of a compound of formula IV with a compound of formula IX is performed first, followed by reaction with hydrazine to form a compound of formula XI, as is shown in Scheme 2.

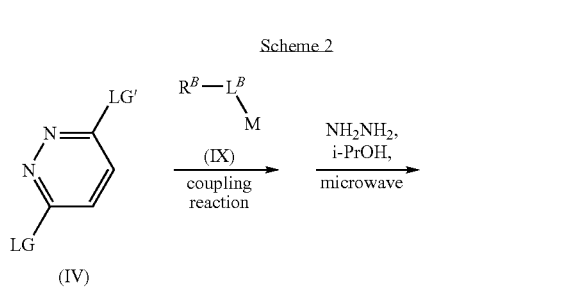

Scheme 2

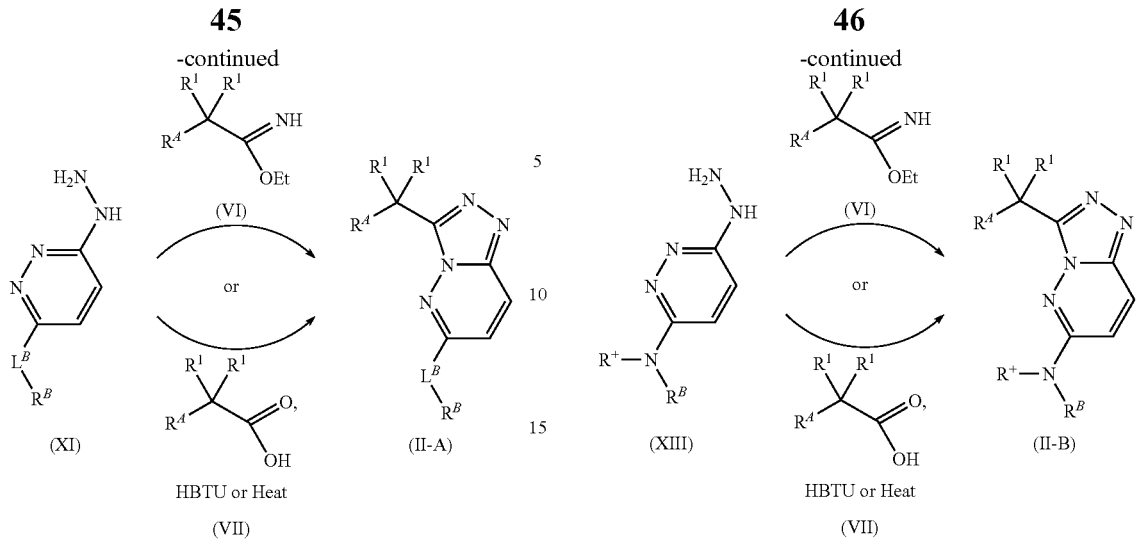

As shown in Scheme 3, either LG or LG' can be reacted first with a nucleophilic moiety, such as, for example, an amine, to form a compound of formula XII, the remaining LG or LG' can then be displaced by hydrazine to form a compound of formula XIII. Reaction of this compound with an imidate ester (or carboxylic acid or carboxylic ester), as described above, then forms a triazolopyridazine having formula II-B.

II. Preparation of Triazolothiadiazoles

As shown in Scheme 4, a carboxylic acid of formula VII can be reacted neat with thiocarbonohydrazide with heating (c. 170° C.) in a condensation reaction to produce a 4-amino-1,2,4-triazole-3-thiol of formula XIV. The compound of formula XIV can be reacted with a carboxylic acid of formula XV in refluxing phosphorus oxychloride to produce a compound of formula III-A, where $L^B$ and $R^B$ is as defined herein for a compound of formula I and $R^A$ is a suitably protected functional group, such as, for example, a hydroxyl, amino, sulfhydryl, carboxyl, or sulfonyl group, that can later be transformed into a nucleophilic group or group suitable for reaction with a nucleophilic group.

To produce a compound of formula III-B, where $R^A$ and $R^B$ are as described above, the compound of formula XIV is reacted with isothiocyante XVI in DMF with heating.

Scheme 3

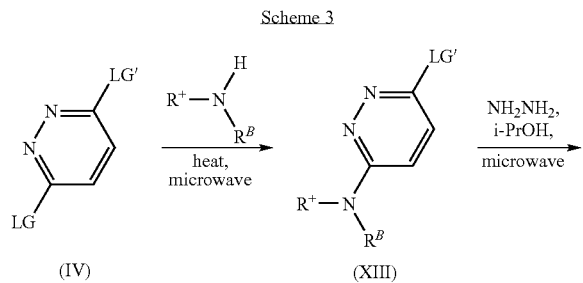

Scheme 4

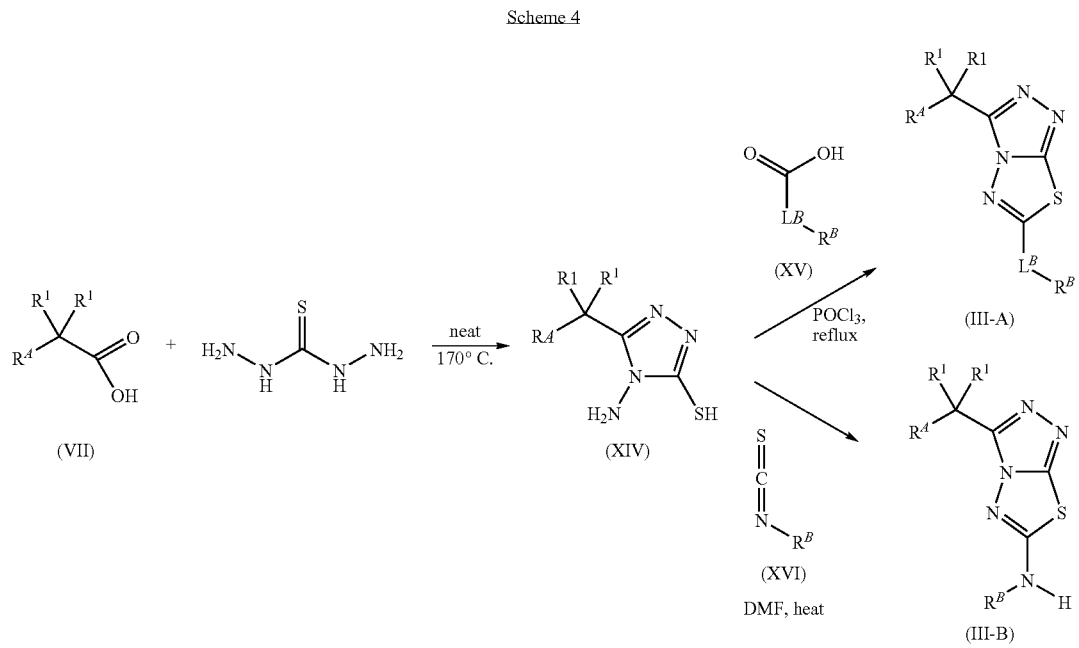

Compounds of formulae II-A, II-B, III-A, or III-B can be further transformed by deprotection and/or activation techniques known to those skilled in the art to produce compounds suitable for further synthetic manipulation, as shown in Scheme 5, where Het represents either the triazolopyridazine heteroaryl ring system of compounds of formula II or the triazolothiadiazole heteroaryl ring system of compounds of formula III.

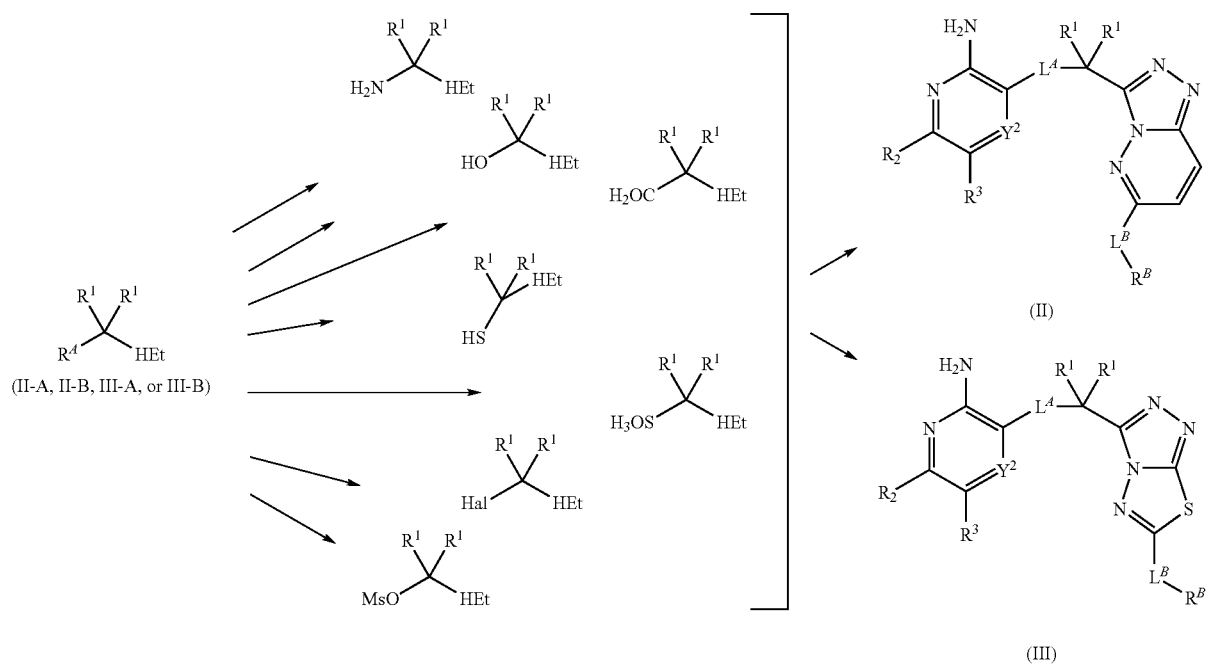

In order that the invention described herein may be more fully understood, the following examples are set forth. It should be understood that these examples are for illustrative purposes only and are not to be construed as limiting this invention in any manner.

Example 1

Preparation of N—((R)-1-(6-(3-chlorophenylamino)-[1,2,4]triazolo[4,3-b]pyridazin-3-yl)ethyl)-3-aminopyrazine-2-carboxamide (Compound XX)

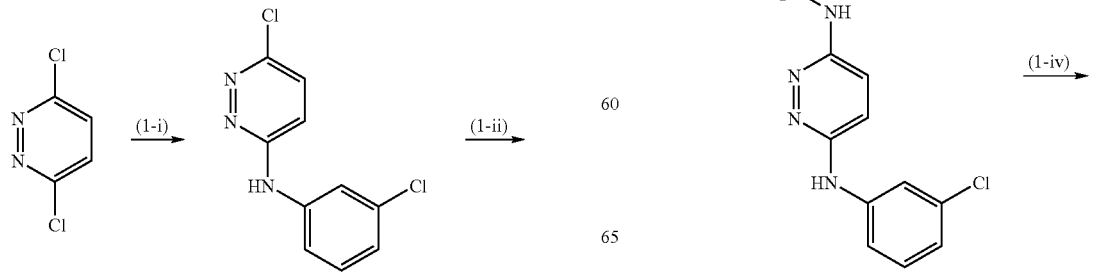

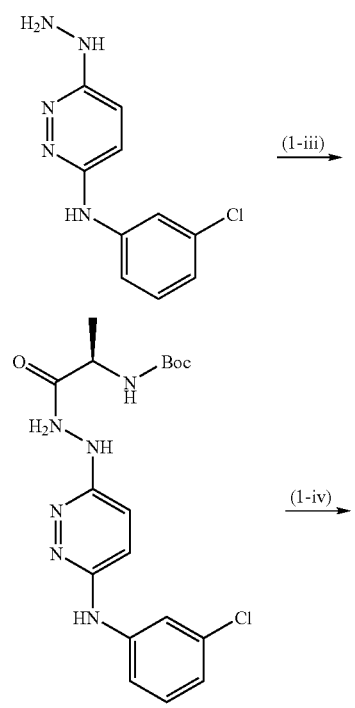

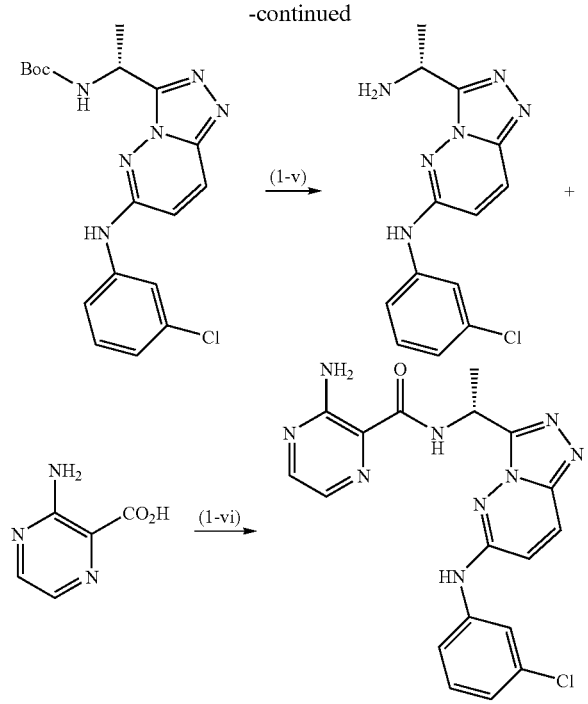

(Step 1-i) 3-Chloroaniline (10 g, 79 mmol) and 3,6-dichloropyridazine (10 g, 68 mmol) were combined in EtOH (50 mL), and the reaction mixture was heated to reflux overnight. The reaction mixture was then diluted with ethyl acetate/saturated sodium bicarbonate (200 mL each), the organic layer dried over sodium sulfate, and the solution concentrated in vacuo to yield a solid. The solid was suspended in $Et_2O$ and the product, 6-chloro-N-(3-chlorophenyl)pyridazin-3-amine, was filtered off as a beige solid (7.7 g, 32 mmol, 47% yield): $^1$H-NMR (500 MHz, DMSO-$d_6$) 9.67 (s, 1H), 8.02 (t, J=2.0 Hz, 1H), 7.62 (d, J=9.3 Hz, 1H), 7.52 (dd, J=1.9, 8.2 Hz, 1H), 7.35 (t, J=8.1 Hz, 1H), 7.23 (d, J=9.3 Hz, 1H), 7.04-7.02 (m, 1H).

(Step 1-ii) 6-chloro-N-(3-chlorophenyl)pyridazin-3-amine (88.1 g, 367 mmol) was suspended in 1:6 triethylene glycol/hydrazine hydrate and heated to reflux for 4 hours. The reaction mixture was cooled to room temperature, diluted with water and a solid filtered off. This solid was triturated with $Et_2O$ to give the product, N-(3-chlorophenyl)-6-hydrazinylpyridazin-3-amine, as a brown solid (60 g, 254 mmol, 69% yield): $^1$H NMR (500 MHz, DMSO-$d_6$) 9.23 (s, 1H), 8.09 (t, J=1.8 Hz, 1H), 7.46 (d, J=8.2 Hz, 1H), 7.24 (t, J=8.1 Hz, 1H), 7.08 (d, J=9.4 Hz, 1H), 7.00 (d, J=9.4 Hz, 1H), 6.85 (dd, J=1.3, 7.8 Hz, 1H).

(Step 1-iii) N-(3-chlorophenyl)-6-hydrazinylpyridazin-3-amine (2.4 g, 10 mmol) was combined with Boc-D-Ala-OH (2.0 g, 10.5 mmol), HBTU (4.4 g, 11.6 mmol) in DMF and DIEA (2.0 mL, 11.5 mmol) was added. The reaction mixture was stirred at room temperature for 2 hours and poured into ethyl acetate/saturated sodium bicarbonate. The organic layer was dried over sodium sulfate, concentrated to an oil, and purified by silica gel column chromatography (EtOAc to 10% MeOH/EtOAc), to give the product, tert-butyl (R)-1-(6-(3-chlorophenylamino)pyridazin-3-ylaminocarbamoyl)ethylcarbamate (1.38 g, 3.4 mmol, 34%).

(Step 1-iv) A solution of tert-butyl (R)-1-(6-(3-chlorophenylamino)pyridazin-3-ylaminocarbamoyl)ethylcarbamate (1.38 g, 3.3 mmol) in 20 mL dioxane was heated to reflux for 16 hrs. The reaction mixture was allowed to cool to room temperature, diluted with 50 mL $Et_2O$, and the product, tert-butyl (R)-1-(6-(3-chlorophenylamino)-[1,2,4]triazolo[4,3-b]pyridazin-3-yl)ethylcarbamate, filtered off as a yellow solid (0.90 g, 2.3 mmol, 70% yield).

(Steps 1-v & 1-yl) tert-Butyl (R)-1-(6-(3-chlorophenylamino)-[1,2,4]triazolo[4,3-b]pyridazin-3-yl)ethylcarbamate (110 mg, 0.28 mmol) was dissolved in 5 mL TFA/$CH_2Cl_2$ (1:1) and left standing for 20 min. The solvent was removed under reduced pressure and $CH_2Cl_2$ was added and removed 4 times to remove residual TFA. The resulting amine was dissolved in DMF and 3-aminopyrazine-2-carboxylic acid (200 mg, 1.4 mmol), HBTU (0.50 g, 1.3 mmol) and DIEA (1 mL, 5.7 mmol) were added. The reaction mixture was stirred at room temperature for 2 hours, then poured into ethyl acetate/0.1 M NaOH. The organic layer was dried over sodium sulfate and concentrated to yield an oil. This oil was purified by reversed-phase HPLC. Fractions containing pure product were concentrated to give N—((R)-1-(6-(3-chlorophenylamino)-[1,2,4]triazolo[4,3-b]pyridazin-3-yl)ethyl)-3-aminopyrazine-2-carboxamide as a yellow solid (60 mg, 0.13 mmol, 48% yield): $^1$H NMR (500 MHz, DMSO-$d_6$) 10.43 (s, 1H), 9.19 (d, J=8.1 Hz, 1H), 8.22-8.20 (m, 2H), 7.89 (t, J=2.0 Hz, 1H), 7.75-7.73 (m, 2H), 7.33 (m, 2H), 7.07 (dd, J=1.3, 7.9 Hz, 1H), 5.76-5.71 (m, 1H), 1.75 (d, J=6.9 Hz, 3H); MH+410.2.

Example 2

Preparation of 1-((R)-1-(6-(3-chlorophenylamino)-[1,2,4]triazolo[4,3-b]pyridazin-3-yl)ethyl)-3-(pyridin-3-yl)urea

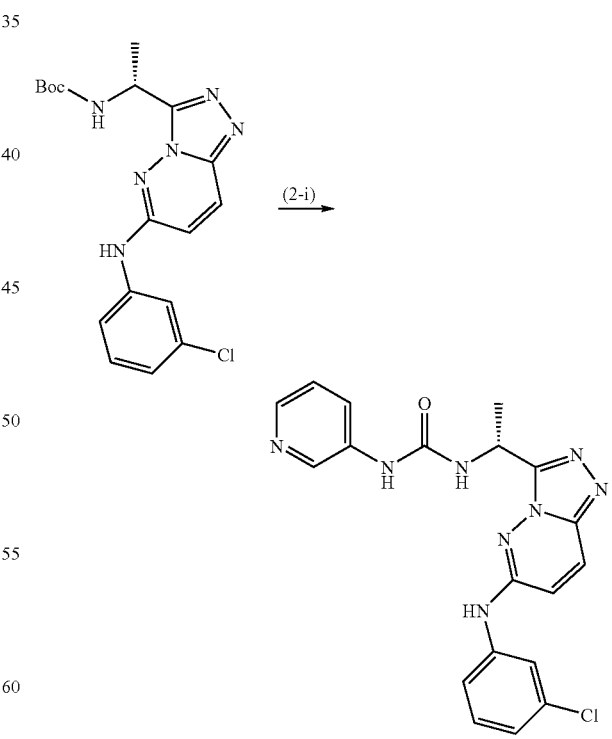

(Step 2-i) tert-Butyl (R)-1-(6-(3-chlorophenylamino)-[1,2,4]triazolo[4,3-b]pyridazin-3-yl)ethylcarbamate (50 mg, 0.13 mmol) was dissolved in 5 mL TFA:$CH_2Cl_2$ (1:1) and left standing for 20 min. The solvent was removed under reduced pressure and CH₂Cl₂ was added and removed 4 times to remove residual TFA. The amine was dissolved in 1 mL NMP and 3-isocyanatopyridine (20 mg, 0.17 mmol) was added followed by the addition of DIEA (0.086 mL, 0.5 mmol). The reaction mixture was microirradiated at 100° C. for 10 min, loaded onto a preparative reversed-phase HPLC column, and the column eluted with a H₂O/CH₃CN 0.1% TFA gradient. Fractions containing pure product were combined and concentrated, 6M HCl was added, and the resulting solution concentrated to give the product, 1-((R)-1-(6-(3-chlorophenylamino)-[1,2,4]triazolo[4,3-b]pyridazin-3-yl)ethyl)-3-(pyridin-3-yl)urea, as the HCl salt (31 mg, 0.076 mmol, 58% yield): ¹H NMR (500 MHz, DMSO-d₆) 10.30 (s, 1H), 10.00 (s, 1H), 9.10 (d, J=2.2 Hz, 1H), 8.45 (d, J=5.4 Hz, 1H), 8.31 (dd, J=1.2, 8.7 Hz, 1H), 8.16 (d, J=9.8 Hz, 1H), 7.94-7.89 (m, 2H), 7.76 (dd, J=1.5, 8.2 Hz, 1H), 7.61 (d, J=7.8 Hz, 1H), 7.36 (t, J=8.1 Hz, 1H), 7.23 (d, J=9.9 Hz, 1H), 7.06 (dd, J=1.4, 8.0 Hz, 1H), 5.52 (t, J=7.3 Hz, 1H), 1.68 (d, J=7.0 Hz, 3H); MH+409.20.

Example 3

Preparation of N-(3-chlorophenyl)-3-(2-(N-((2-aminopyridin-3-yl)methyl)-N-(methyl)amino)methyl)-[1,2,4]triazolo[4,3-b]pyridazin-6-amine

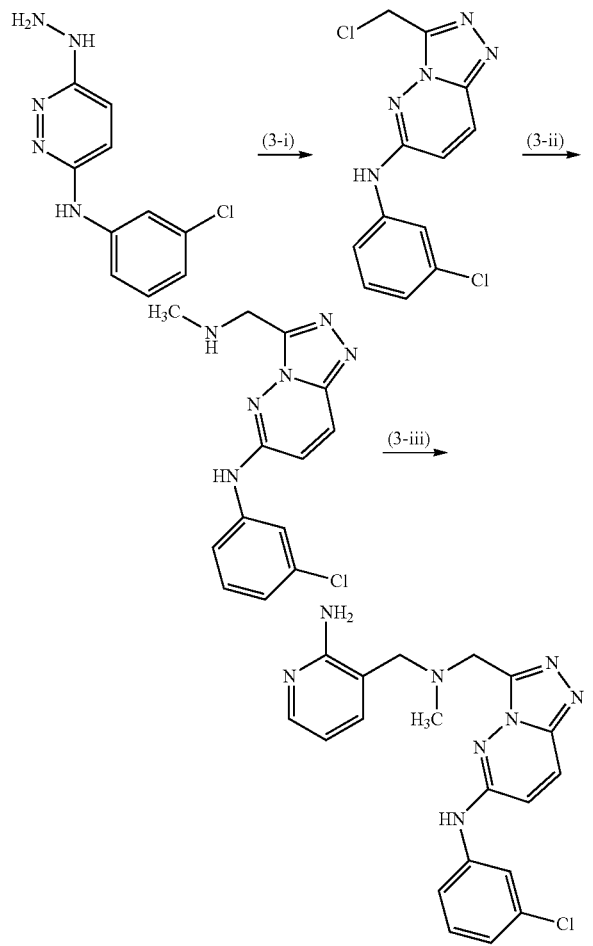

(Step 3-i) N-(3-chlorophenyl)-6-hydrazinylpyridazin-3-amine (4.0 g, 17 mmol)) was taken up in HCl/Et₂O (20 mL) and stirred for 10 min. The reaction mixture was concentrated, taken up in DMF (20 mL), and 2-chloro-1,1,1-trimethoxyethane (5.2 g, 34 mmol) was added. After stirring for 3 hours, a precipitate began to form. After one hour additional stirring, the reaction mixture was filtered to give the product, 3-(chloromethyl)-N-(3-chlorophenyl)-[1,2,4]triazolo[4,3-b]pyridazin-6-amine, as a white solid. (4 g, 13.6 mmol, 80% yield): ¹H-NMR (500 MHz, DMSO-d₆) 10.40 (s, 1H), 8.19 (d, J=9.8 Hz, 1H), 8.13 (t, J=1.8 Hz, 1H), 7.68 (dd, J=1.7, 8.2 Hz, 1H), 7.40 (t, J=8.1 Hz, 1H), 7.28 (d, J=9.9 Hz, 1H), 7.11-7.09 (m, 1H).

(Step 3-ii) 3-(Chloromethyl)-N-(3-chlorophenyl)-[1,2,4]triazolo[4,3-b]pyridazin-6-amine (210 mg, 0.71 mmol) was suspended in 2 mL of 40% methyl amine in water and the suspension microirradiated at 100° C. for 10 min. The reaction mixture was allowed to cool to room temperature and a brown solid was filtered off and dried in vacuo to yield the product, N-(3-chlorophenyl)-3-((methylamino)methyl)-[1,2,4]triazolo[4,3-b]pyridazin-6-amine (126 mg, 0.43 mmol, 61% yield): MH+=289.02.

(Step 3-iii) N-(3-chlorophenyl)-3-((methylamino)methyl)-[1,2,4]triazolo[4,3-b]pyridazin-6-amine (40 mg, 0.14 mmol) was combined with 2-aminopyridine-3-carboxaldehyde (20 mg, 0.16 mmol) in methanol (1 mL) and acetic acid (5 drops). To this solution was added NaCNBH₃ (60 mg, 0.43 mmol) as a solid in two portions. After 1 hr, 20 mg more aldehyde was added, followed by the addition of 30 mg more NaCNBH₃. The reaction mixture was stirred overnight, followed by concentration in vacuo to yield a solid. The solid was taken up in NMP, filtered and purified by reversed-phase HPLC. Concentration of the fractions containing pure product gave a solid, which was treated with 6N HCl and concentrated in vacuo to give the product, N-(3-chlorophenyl)-3-(2-(N-((2-aminopyridin-3-yl)methyl)-N-(methyl)amino)methyl)-[1,2,4]triazolo[4,3-b]pyridazin-6-amine, as the bis-HCl salt (21 mg, 0.045 mmol, 34% yield): ¹H-NMR (500 MHz, DMSO-d₆) 10.45 (s, 1H), 8.22 (d, J=9.8 Hz, 2H), 8.16 (d, J=5.7 Hz, 1H), 8.02 (d, J=6.0 Hz, 1H), 7.93 (s, 1H), 7.76 (d, J=8.2 Hz, 1H), 7.42 (t, J=8.1 Hz, 1H), 7.30 (d, J=9.9 Hz, 1H), 7.10 (dd, J=1.6, 7.9 Hz, 1H), 6.91 (t, J=6.8 Hz, 1H), 4.68 (s, 2H), 4.28 (s, 2H), 2.70 (s, 3H); MH+395.17.

Example 4

Preparation of 3-(((pyridin-3-yl)methoxy)methyl)-N-(3-chlorophenyl)-[1,2,4]triazolo[4,3-b]pyridazin-6-amine

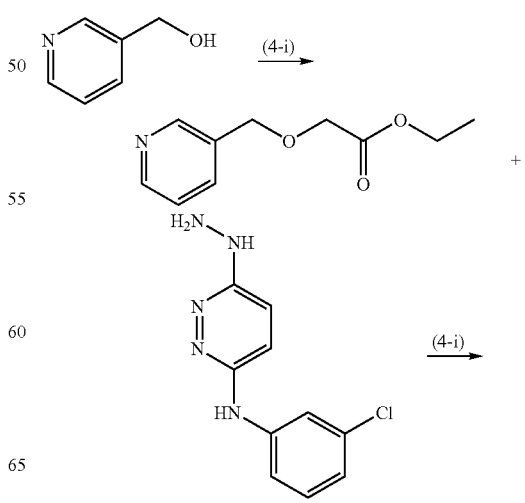

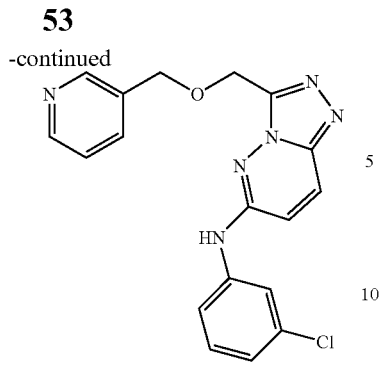

(Step 4-i) Sodium hydride (60%) (0.44 g, 11 mmol) was added to a solution of (pyridin-3-yl)methanol (1.09 g, 10 mmol) in THF. The reaction mixture was stirred at room temperature for 10 min and ethyl bromoacetate (1.8 g, 11 mmol) was added, followed by the addition of 20 mg of tetrabutyl ammonium iodide. The reaction mixture was stirred overnight, diluted with ethyl acetate/saturated sodium bicarbonate, and the organic layer was dried over sodium sulfate. The solution was concentrated to an oil, which was purified by silica gel column chromatography to give the product, ethyl 2-((pyridin-3-yl)methoxy)acetate, as a brown oil (0.63 g, 3.2 mmol, 32% yield): $^1$H-NMR (500 MHz, DMSO-d$_6$) 8.63 (d, J=1.8 Hz, 1H), 8.59 (dd, J=1.5, 4.8 Hz, 1H), 7.79 (d, J=7.8 Hz, 1H), 7.34 (dd, J=4.9, 7.7 Hz, 1H), 4.68 (s, 2H), 4.26 (q, J=7.1 Hz, 2H), 4.15 (s, 2H), 1.32 (t, J=7.1 Hz, 3H).

(Step 4-ii) Ethyl 2-((pyridin-3-yl)methoxy)acetate (65 mg, 0.33 mmol) and N-(3-chlorophenyl)-6-hydrazinylpyridazin-3-amine (60 mg, 0.25 mmol) were combined in a 16×100 mm test tube and placed into a 160° C. oil bath for 15 min. The residue was dissolved in 1 mL DMSO and purified by reversed-phase HPLC. Fractions containing pure product were concentrated in vacuo to yield a solid, dissolved in HCl/methanol, and concentrated in vacuo to give the yellow solid product, 3-(((pyridin-3-yl)methoxy)methyl)-N-(3-chlorophenyl)-[1,2,4]triazolo[4,3-b]pyridazin-6-amine, as an HCl salt (22 mg, 0.055 mmol, 22% yield). $^1$H-NMR (500 MHz, DMSO-d6) 10.25 (s, 1H), 8.80 (s, 1H), 8.77 (d, J=5.2 Hz, 1H), 8.40 (d, J=8.1 Hz, 1H), 8.16 (d, J=9.9 Hz, 1H), 8.07 (t, J=2.0 Hz, 1H), 7.90 (dd, J=5.6, 7.9 Hz, 1H), 7.61 (dd, J=2.0, 8.2 Hz, 1H), 7.36 (t, J=8.1 Hz, 1H), 7.20 (d, J=9.9 Hz, 1H), 7.08-7.06 (m, 1H), 5.11 (s, 2H), 4.89 (s, 2H); MH+367.3.

Example 5

Preparation of 2-(6-(3-chlorophenylamino)-[1,2,4]triazolo[4,3-b]pyridazin-3-yl)-N-(pyridin-3-yl)acetamide

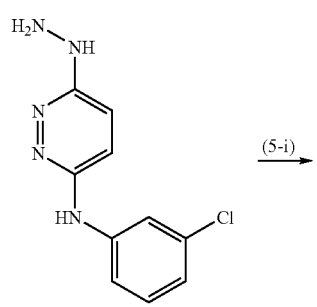

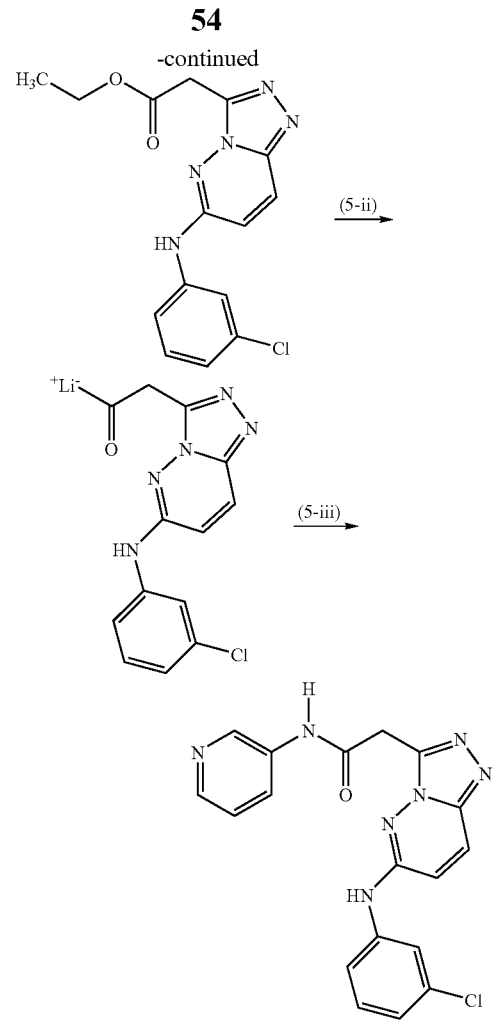

(Step 5-i) N-(3-chlorophenyl)-6-hydrazinylpyridazin-3-amine (1 g, 4.25 mmol)) was taken up in ethanol (10 mL) and diethyl malonate (2 g, 12.76 mmol) was added. After microirradiation at 150° C. for 30 min, the reaction mixture was concentrated to dryness, taken up in ethyl acetate, and filtered to give the product, ethyl 2-(6-(3-chlorophenylamino)-[1,2,4]triazolo[4,3-b]pyridazin-3-yl)acetate, as a solid (1.1 g, 3.3 mmol, 78% yield).

(Step 5-ii) Ethyl 2-(6-(3-chlorophenylamino)-[1,2,4]triazolo[4,3-b]pyridazin-3-yl)acetate (1 g, 3 mmol)) was treated with LiOH (72.0 mg 3 mmol)) in 1:1 THF:H$_2$O at 60° C. for 6 hours. The reaction mixture was concentrated to dryness and taken up in methanol and the product, lithium 2-(6-(3-chlorophenylamino)-[1,2,4]triazolo[4,3-b]pyridazin-3-yl)acetate, filtered off as a white solid (600 mg, 1.9 mmol, 63% yield).

Lithium 2-(6-(3-chlorophenylamino)-[1,2,4]triazolo[4,3-b]pyridazin-3-yl)acetate (50 mg, 0.16 mmol) is taken up in DMF (3 ml) and EDCI (45 mg, 0.24 mmol), HOBt (32 mg, 0.24 mmol), Et$_3$N (30 ul, 0.32 mmol), and 3-aminopyridine is added. The reaction mixture is stirred at 60° C. overnight. The reaction mixture is diluted with ethyl acetate, washed with water, and the organic layer concentrated to dryness. Purification by reversed-phase HPLC yields the product, 2-(6-(3-chlorophenylamino)-[1,2,4]triazolo[4,3-b]pyridazin-3-yl)-N-(pyridin-3-yl)acetamide.

III. Intermediates Useful for Suzuki Coupling

During the preparation of some compounds of the invention, useful intermediates can be prepared by coupling a metallated/boronated moiety with an aryl halide. A particularly facile method is the reaction of an aryl boronic acid or boronate moiety with an aryl halide, such as, for example, an aryl chloride, bromide, or iodide. This method is known to one skilled in the art as the Suzuki reaction and is described in U.S. Pat. Nos. 6,939,985 and 6,559,310, and in U.S. Patent Application No. 20040133028. For the preparation of compounds of the invention, one particularly useful aryl halide intermediate for this reaction, methyl 2-amino-5-bromopyridine-3-carboxylate, can be purchased from Bionet, Inc. Two other useful intermediates, methyl 3-amino-6-bromopyrazine-2-carboxylate and 5-bromo-1H-pyrazolo[3,4-b]pyridin-3-amine, are prepared as described in Examples 6 and 7, respectively. An example of the use of the Suzuki reaction to prepare a compound of the invention is provided below in Example 8.

Example 6

Preparation of Methyl 3-amino-6-bromopyrazine-2-carboxylate

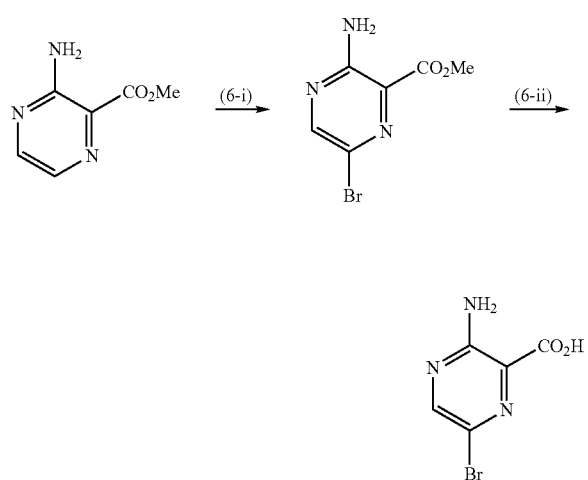

(Step 6-i) To a solution of methyl 3-aminopyrazine-2-carboxylate (5 g, 32.65 mmol) in 20 mL warm acetic acid was added to 2.8 mL of bromine dropwise. The reaction mixture was allowed to stand for 10 min, then added to 150 mL of water. The precipitate was collected and washed with water. After drying in vacuo, the resulting orange solid, methyl 3-amino-6-bromopyrazine-2-carboxylate, can be used directly without further purification.

(Step 6-ii) To a solution of methyl 3-amino-6-bromopyrazine-2-carboxylate (1 g, 4.33 mmol) in 10 mL THF was added a solution of LiOH (540 mg, 12.86 mmol) in 20 mL of water. The mixture was stirred at room temperature for 4 hours and acidified with 6M HCl to a pH of 2. The yellow precipitate was collected by filtration and washed with water. After drying in vacuo, the product, 3-amino-6-bromopyrazine-2-carboxylic acid (600 mg, 2.75 mmol, 64% yield), can be used directly in the next reaction without further purification.

Example 7

Preparation of 5-bromo-1H-pyrazolo[3,4-b]pyridin-3-amine

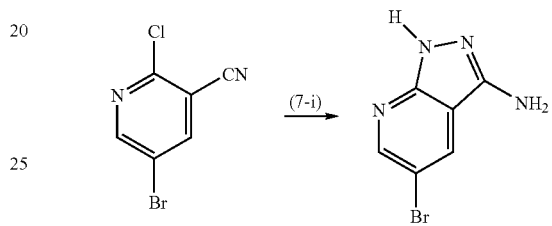

(Step 7-i) To a solution of 5-bromo-2-chloropyridine-3-carbonitrile (2 g, 9.22 mmol) in 30 mL n-butanol was added 2 mL anhydrous hydrazine. The reaction mixture was heated under reflux for 14 hrs and allowed to cool to room temperature. The solvent was removed by evaporation and the residue was poured into a saturated NaHCO$_3$ solution. The resulting precipitate was collected and washed with water. After drying in vacuo, the product, 5-bromo-1H-pyrazolo[3,4-b]pyridin-3-amine, can be used directly without further purification.

Example 8

Preparation of (R)-3-(1-aminoethyl)-N-(3-chlorophenyl)-[1,2,4]triazolo[3,4-b][1,3,4]thiadiazol-6-(furan-3-yl)pyrazine-2-carboxamide

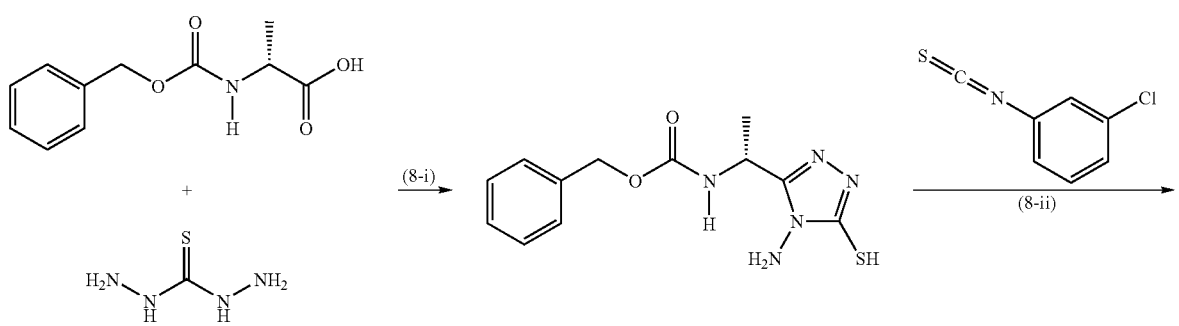

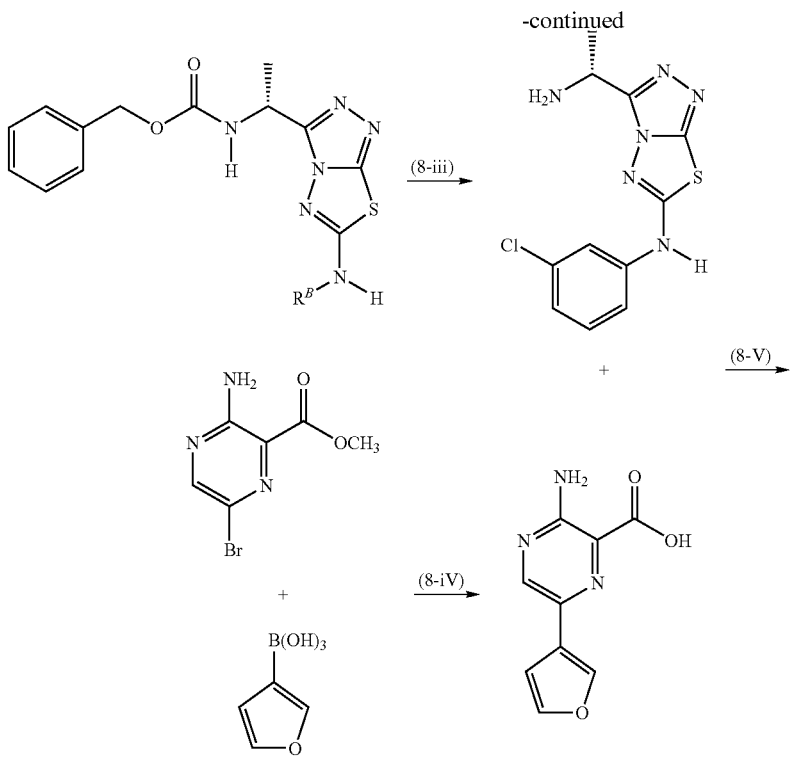
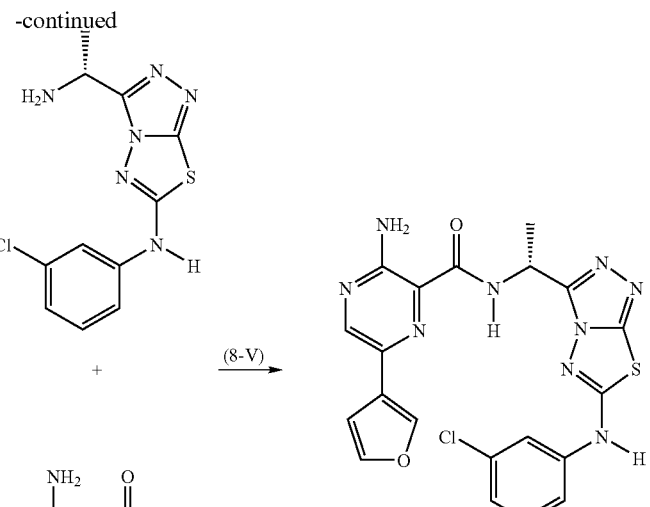

(Step 8-i) A well-blended neat mixture of Cbz-D-Ala-OH (15 g, 67.2 mmol) and thiosemicarbazide (7.135 g, 67.2 mmol) was rapidly brought to 172° C. After 15 minutes the heat was removed and, while the mixture was still hot, water (200 mL) was added. After stirring for 2 hours the resulting slurry was filtered and washed with water. The collected solids were dried in vacuo overnight to provide 14 g as a white solid. This material was slurried in Et$_2$O (200 mL), filtered, and dried in vacuo to provide 11.0 g of —(R)-benzyl 1-(5-mercapto-4-amino-4H-1,2,4-triazol-3-yl)ethylcarbamate as a white solid: ESMS MH+=294.

(Step 8-ii) A mixture of (R)-benzyl 1-(5-mercapto-4-amino-4H-1,2,4-triazol-3-yl)ethylcarbamate (1.32 g, 4.5 mmol) in ethanol (15 mL) was heated to 80° C. and 3-chlorophenylisothiocyanate (1.3 g, 7.65 mmol) and dicyclohexylcarbodiimide (1.11 g, 5.4 mmol) were added. After 4 hours, the reaction was cooled, diluted with an equal volume of ether, and filtered. The filter cake was washed with additional ether and the collected solids dried in vacuo to provide 0.94 g of (R)-benzyl 1-(6-(3-chlorophenylamino)-[1,2,4]triazolo[3,4-b][1,3,4]thiadiazol-3-yl)ethylcarbamate: ESMS MH+=429.

(Step 8-iii) To a slurry of (R)-benzyl 1-(6-(3-chlorophenylamino)-[1,2,4]triazolo[3,4-b][1,3,4]thiadiazol-3-yl)ethylcarbamate (0.39 g, 0.92 mmol) in acetic acid (20 mL) was added 48% hydrobromic acid in water (10 mL). The mixture was heated to 90° C. for 2 hours. After cooling to room temperature, the resulting solution was concentrated to ⅓ the original volume, poured on ice and the pH adjusted to 8 with 2N sodium hydroxide. The resulting precipitate was filtered, washed with water, and dried overnight in vacuo to provide (R)-3-(1-aminoethyl)-N-(3-chlorophenyl)-[1,2,4]triazolo[3,4-b][1,3,4]thiadiazol-6-amine (0.19 g): ESMS MH+=294.

(Step 8-iv) Methyl 3-amino-6-bromopyrazine-2-carboxylate (700 mg, 3 mmol) was dissolved in dioxane (4 mL) with 3-furan boronic acid (0.36 g, 3.2 mmol), potassium acetate (980 mg 10 mmol) and tetrakispalladium triphenylphosphine (200 mg, 0.17 mmol) in a microwave vessel. Nitrogen was bubbled through for 5 minutes, followed by sealing the vessel and microirradiating the mixture for 20 minutes at 170° C. The reaction mixture was diluted with ethyl acetate/saturated sodium bicarbonate, dried over sodium sulfate, and concentrated to give a solid, which was purified by silica gel column chromatography (0 to 70% EtOAc/hexanes) to give methyl 3-amino-6-(furan-3-yl)pyrazine-2-carboxylate as a solid. This methyl ester was dissolved in THF/MeOH and an aqueous solution of LiOH hydrate (150 mg, 3.6 mmol) was added. The reaction mixture was stirred for 1 hour at room temperature, concentrated to half the volume, and diluted with ethyl acetate/10% aqueous citric acid solution. The organic layer was washed with brine, dried, and concentrated in vacuo to yield 3-amino-6-(furan-3-yl)pyrazine-2-carboxylic acid as a solid (0.46 g, 2.3 mmol, 77% overall yield).

(Step 8-v) To a mixture of (R)-3-(1-aminoethyl)-N-(3-chlorophenyl)-[1,2,4]triazolo[3,4-b][1,3,4]thiadiazol-6-amine (0.141 g, 0.483 mmol) in DMF (3 mL) was added 3-amino-6-(furan-3-yl)pyrazine-2-carboxylic acid (0.066 g, 0.322 mmol), HBTU (0.159 g, 0.42 mmol), and TEA (0.135 ml, 0.966 mmol). After two hours the mixture was diluted with water and the resulting solids were collected. The solids were washed sequentially with 20% ethanol/ethyl ether, methylene chloride, and methanol, then dried in vacuo to provide (R)-3-(1-aminoethyl)-N-(3-chlorophenyl)-[1,2,4]triazolo[3,4-b][1,3,4]thiadiazol-6-(furan-3-yl)pyrazine-2-carboxamide (0.09 g): $^1$H NMR 300 MHz DMSO-d$_6$ 10.8 (s, 1H), 9.21 (s, 1H), 8.61 (s, 1H), 8.38 (s, 1H), 7.68 (s, 1H), 7.51 (s, 1H), 7.39 (d, 2H), 7.13 (m, 3H), 7.05 (d, 2H), 5.69 (m, 1H), 1.76 (d, 3H); ESMS MH+=482.

Biological Assay of Compounds of the Invention

Example 9

$K_i$ Determination for the Inhibition of c-Met

Compounds of the invention were screened for their ability to inhibit c-Met kinase activity using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 μL per well containing 1.0 nM c-Met, 100 mM HEPES (pH 7.5), 10 mM MgCl$_2$, 25 mM NaCl, 0.01% BSA, 1 mM DTT, 0.5 mg/mL polyE4Y, and 35 μM ATP. Accordingly, compounds of the invention were dissolved in DMSO to make 10 mM initial stock solutions. Serial dilutions in DMSO were then made to obtain the final solutions for the assay. A 1.5 μL aliquot of DMSO or inhibitor in DMSO was added to each well. The reaction was initiated by the addition of $^{33}$P-ATP and polyE4Y (obtained from Sigma). After 20 min, the reaction was quenched with 50 μL of 30% trichloroacetic acid (TCA) containing 4 mM ATP. The reaction mixture was transferred to the 0.66 mm GF filter plates (Corning) and washed three times with 5% TCA. Following the addition of 50 μL of Ultimate Gold™ high efficiency scintillant (Packard Bioscience), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. Selected $K_i$ values are provided in Table 2, where "A" represents a $K_i$ of 0.25 μM or less, "B" represents a $K_i$ of greater than 0.25 μM and less than or equal to 2.5 μM, and "C" represents a $K_i$ value of greater than 2.5 μM.

TABLE 2

| Compound No. | c-Met Ki (μM) | ESMS (M + H) | HPLC R$_t$ (min.) | $^1$H NMR (500 MHz) NMR peaks given as δ values |
|---|---|---|---|---|
| 1 | A | 380.10 | 1.60 | |
| 2 | A | 367.30 | 1.84 | DMSO-d$_6$ (500 MHz) 10.25 (s, 1H), 8.80 (s, 1H), 8.77 (d, J = 5.2 Hz, 1H), 8.40 (d, J = 8.1 Hz, 1H), 8.16 (d, J = 9.9 Hz, 1H), 8.07 (t, J = 2.0 Hz, 1H), 7.90 (dd, J = 5.6, 7.9 Hz, 1H), 7.61 (dd, J = 2.0, 8.2 Hz, 1H), 7.36 (t, J = 8.1 Hz, 1H), 7.20 (d, J = 9.9 Hz, 1H), 7.08-7.06 (m, 1H), 5.11 (s, 2H), 4.89 (s, 2H) |
| 3 | C | 366.10 | 1.80 | |
| 4 | C | 366.10 | 1.50 | |
| 5 | C | 381.00 | 1.95 | |
| 6 | C | 394.10 | 1.51 | |
| 7 | C | 394.00 | 2.14 | |
| 8 | B | 395.10 | 1.60 | |
| 9 | C | 394.10 | 1.60 | |
| 10 | C | 394.17 | 2.13 | DMSO-d$_6$ (500 MHz) 10.33 (s, 1H), 9.51 (d, J = 7.3 Hz, 1H), 9.17 (d, J = 1.6 Hz, 1H), 8.84 (dd, J = 1.0, 5.1 Hz, 1H), 8.55 (d, J = 8.0 Hz, 1H), 8.18 (d, J = 9.9 Hz, 1H), 7.81-7.76 (m, 3H), 7.28-7.20 (m, 2H), 7.07-6.99 (m, 1H), 5.79 (qn, J = 7.0 Hz, 1H), 1.78 (d, J = 7.0 Hz, 3H) |
| 11 | B | 395.17 | 1.77 | DMSO-d$_6$ (500 MHz) 10.45 (s, 1H), 8.22 (d, J = 9.8 Hz, 2H), 8.16 (d, J = 5.7 Hz, 1H), 8.02 (d, J = 6.0 Hz, 1H), 7.93 (s, 1H), 7.76 (d, J = 8.2 Hz, 1H), 7.42 (t, J = 8.1 Hz, 1H), 7.30 (d, J = 9.9 Hz, 1H), 7.10 (dd, J = 1.6, 7.9 Hz, 1H), 6.91 (t, J = 6.8 Hz, 1H), 4.68 (s, 2H), 4.28 (s, 2H), 2.70 (s, 3H) |
| 12 | C | 394.14 | 2.10 | |
| 13 | B | 409.40 | 1.80 | DMSO-d$_6$ (500 MHz) 9.90 (s, 1H), 9.36 (d, J = 6.9 Hz, 1H), 8.30 (d, J = 6.8 Hz, 1H), 8.15-8.10 (m, 3H), 7.82 (t, J = 2.0 Hz, 1H), 7.67 (dd, J = 1.5, 8.3 Hz, 1H), 7.30 (t, J = 8.1 Hz, 1H), 7.06-7.02 (m, 2H), 6.83-6.81 (m, 1H), 5.72 (t, J = 7.1 Hz, 1H), 1.74 (d, J = 7.0 Hz, 3H) |
| 14 | A | 410.20 | 2.48 | DMSO-d$_6$ (500 MHz) 10.43 (s, 1H), 9.19 (d, J = 8.1 Hz, 1H), 8.22-8.20 (m, 2H), 7.89 (t, J = 2.0 Hz, 1H), 7.75-7.73 (m, 2H), 7.33 (m, 2H), 7.07 (dd, J = 1.3, 7.9 Hz, 1H), 5.76-5.71 (m, 1H), 1.75 (d, J = 6.9 Hz, 3H) |
| 15 | B | 409.20 | 1.75 | DMSO-d$_6$ (500 MHz) 10.30 (s, 1H), 10.00 (s, 1H), 9.10 (d, J = 2.2 Hz, 1H), 8.45 (d, J = 5.4 Hz, 1H), 8.31 (dd, J = 1.2, 8.7 Hz, 1H), 8.16 (d, J = 9.8 Hz, 1H), 7.94-7.89 (m, 2H), 7.76 (dd, J = 1.5, 8.2 Hz, 1H), 7.61 (d, J = 7.8 Hz, 1H), 7.36 (t, J = 8.1 Hz, 1H), 7.23 (d, J = 9.9 Hz, 1H), 7.06 (dd, J = 1.4, 8.0 Hz, 1H), 5.52 (t, J = 7.3 Hz, 1H), 1.68 (d, J = 7.0 Hz, 3H) |

TABLE 2-continued

| Compound No. | c-Met Ki (μM) | ESMS (M + H) | HPLC R$_t$ (min.) | ¹H NMR (500 MHz) NMR peaks given as δ values |
|---|---|---|---|---|
| 16 | B | 445.20 | 2.78 | DMSO-d$_6$ (500 MHz) 10.14 (s, 1H), 9.54 (d, J = 8.1 Hz, 1H), 9.50 (s, 1H), 8.17 (d, J = 9.8 Hz, 2H), 8.03-7.91 (m, 3H), 7.84 (t, J = 1.9 Hz, 1H), 7.76 (dd, J = 1.5, 8.2 Hz, 1H), 7.32 (t, J = 8.1 Hz, 1H), 7.16 (d, J = 9.9 Hz, 1H), 7.02 (dd, J = 1.4, 7.9 Hz, 1H), 5.88-5.85 (m, 1H), 1.83 (d, J = 7.0 Hz, 3H) |
| 17 | B | 487.04 | 2.62 | DMSO-d$_6$ (500 MHz) 10.23 (s, 1H), 9.20 (d, J = 7.3 Hz, 1H), 8.25 (d, J = 2.3 Hz, 1H), 8.19-8.16 (m, 2H), 7.83 (t, J = 1.9 Hz, 1H), 7.75 (d, J = 8.3 Hz, 1H), 7.30 (t, J = 8.1 Hz, 1H), 7.22 (d, J = 9.8 Hz, 1H), 7.04 (d, J = 8.0 Hz, 1H), 5.72 (qn, J = 7.1 Hz, 1H), 1.73 (d, J = 7.0 Hz, 3H) |
| 18 | B | 488.00 | 2.80 | DMSO-d$_6$ (500 MHz) 10.29 (s, 1H), 9.09 (d, J = 8.1 Hz, 1H), 8.34 (s, 1H), 8.19 (d, J = 9.8 Hz, 1H), 7.88 (t, J = 2.0 Hz, 1H), 7.72 (d, J = 8.2 Hz, 1H), 7.34 (t, J = 8.1 Hz, 1H), 7.27-7.25 (m, 1H), 7.06 (dd, J = 1.3, 7.9 Hz, 1H), 5.77-5.71 (m, 1H), 1.75 (d, J = 7.0 Hz, 3H) |
| 19 | C | 368.10 | 2.33 | DMSO-d$_6$ (500 MHz) 9.96 (s, 1H), 8.66 (d, J = 0.9 Hz, 1H), 8.57-8.54 (m, 2H), 8.15 (d, J = 9.8 Hz, 1H), 8.05 (t, J = 2.0 Hz, 1H), 7.59 (dd, J = 1.4, 8.3 Hz, 1H), 7.36 (t, J = 8.1 Hz, 1H), 7.08-7.06 (m, 2H), 5.11 (s, 2H), 4.85 (s, 2H) |
| 20 | A | 392.2 | 2.18 | |
| 21 | A | 486.20 | 2.98 | |
| 22 | A | 543.50 | 2.40 | |
| 23 | A | 485.50 | 2.70 | |
| 24 | A | 542.50 | 2.30 | |
| 25 | B | 432.50 | 2.70 | |
| 26 | B | 489.60 | 2.30 | |
| 27 | A | 490.30 | 2.40 | |
| 28 | B | 486.30 | 3.00 | |
| 29 | A | 492.14 | 2.94 | |
| 30 | A | 502.20 | 2.60 | |
| 31 | A | 492.20 | 2.89 | |
| 32 | A | 476.30 | 2.79 | |
| 33 | A | 476.20 | 3.10 | DMSO-d$_6$ (300 MHz): 9.95 (s, 1H), 9.05 (d, 1H), 8.41 (s, 1H), 8.15 (d, 1H), 7.91 (s, 1H), 7.66-7.55 (m, 3H), 7.35 (t, 1H), 7.05 (d, 2H), 6.42 (s, 1H), 5.82 (t, 1H), 2.45 (br, 4H), 1.85 (m, 5H) |
| 34 | B | 500.20 | 3.14 | |
| 35 | C | 514.20 | 3.32 | |
| 36 | A | 434.10 | 2.70 | DMSO-d$_6$ (300 MHz): 10.00 (br, 1H), 9.09 (d, 1H), 8.34 (s, 1H), 8.13 (d, 1H), 7.86 (s, 2H), 7.68 (d, 1H), 7.33 (t, 1H), 7.05 (m, 2H), 5.12 (m, 1H), 4.27 (s, 1H), 1.73 (d, 3H) |
| 37 | A | 436.10 | 2.70 | DMSO-d$_6$ (300 MHz): 9.95 (s, 1H), 9.18 (d, 1H), 8.35 (s, 1H), 8.14 (d, 1H), 7.88 (s, 1H), 7.67 (d, 1H), 7.34 (t, 1H), 7.05 (d, 2H), 6.56 (dd, 1H), 6.05 (d, 1H), 5.78 (m, 1H), 5.20 (d, 1H), 1.77 (d, 3H) |
| 38 | A | 435.10 | 2.60 | DMSO-d$_6$ (300 MHz): 9.92 (s, 1H), 9.37 (d, 1H), 8.64 (s, 1H), 8.60 (s, 1H), 8.37 (br, 1H), 8.14 (d, 1H), 7.85 (t, 1H), 7.66 (dd, 1H), 7.32 (t, 1H), 7.02 (s, 1H), 7.00 (s, 1H), 5.72 (m, 1H), 1.76 (d, 3H) |
| 39 | A | 453.10 | 2.20 | DMSO-d$_6$ (300 MHz): 9.89 (s, 1H), 9.68 (d, 1H), 8.69 (s, 1H), 8.51 (brs, 2H), 8.15 (br, 1H), 7.95 (s, 1H), 7.77-7.75 (m, 2H), 7.37 (s, 1H), 7.28 (t, 1H), 7.03 (m, 2H), 5.87 (m, 1H), 1.76 (d, 3H) |
| 40 | A | 478.20 | 3.10 | DMSO-d$_6$ (300 MHz): 10.0 (br, 1H), 9.00 (d, 1H), 8.15 (m, 2H), 8.00 (s, 1H), 7.62 (d, 1H), 7.34 (m, 3H), 7.05 (d, 1H), 5.73 (m, 1H), 2.89 (m, 1H), 1.81 (m, 2H), 1.76 (d, 3H), 1.54 (m, 6H) |

TABLE 2-continued

| Compound No. | c-Met Ki (μM) | ESMS (M + H) | HPLC R_t (min.) | ¹H NMR (500 MHz) NMR peaks given as δ values |
|---|---|---|---|---|
| 41 | A | 487.10 | 1.90 | DMSO-$d_6$ (300 MHz): 10.42 (s, 1H), 9.59 (s, 2H), 9.17 (d, 1H), 9.05 (s, 1H), 8.79 (d, 1H), 8.20 (d, 1H), 8.03 (dd, 1H), 7.84 (s, 1H), 7.74 (d, 1H), 7.32 (d, 1H), 7.25 (t, 1H), 6.97 (d, 1H), 5.92 (m, 1H), 1.83 (d, 3H) |
| 42 | A | 487.10 | 1.80 | DMSO-$d_6$ (300 MHz): 10.56 (s, 1H), 9.61 (d, 1H), 9.22 (s, 1H), 8.84 (d, 2H), 8.72 (d, 2H), 8.20 (d, 1H), 7.86 (s, 1H), 7.74 (d, 1H), 7.36 (d, 1H), 7.25 (t, 1H), 6.96 (d, 1H), 5.87 (m, 1H), 1.83 (d, 3H) |
| 43 | A | 464.20 | 2.40 | DMSO-$d_6$ (300 MHz): 10.07 (s, 1H), 9.08 (d, 1H), 8.33 (s, 1H), 8.18 (m, 1H), 7.86 (s, 1H), 7.69 (d, 1H), 7.36 (t, 1H), 7.07 (m, 2H), 5.71 (m, 1H), 4.27 (s, 2H), 1.73 (d, 3H) |
| 44 | A | 478.20 | 2.40 | DMSO-$d_6$ (300 MHz): 9.94 (s, 1H), 9.03 (m, 1H), 8.25 (s, 1H), 7.85 (s, 1H), 7.73 (d, 1H), 7.39 (t, 1H), 7.05 (m, 2H), 5.67 (m, 1H), 4.12 (t, 2H, covered by H2O), 3.55 (t, 2H), 1.73 (d, 3H) |
| 45 | B | 518.20 | 2.70 | DMSO-$d_6$ (300 MHz): 9.94 (s, 1H), 9.02 (d, 1H), 8.29 (s, 1H), 8.15 (m, 1H), 7.86 (t, 1H), 7.68 (d, 1H), 7.34 (t, 1H), 7.05 (d, 1H), 5.73 (m, 1H), 1.85-1.67 (m, 11H) |
| 46 | A | 492.20 | 2.60 | DMSO-$d_6$ (300 MHz): 9.95 (s, 1H), 9.04 (d, 1H), 8.28 (s, 1H), 8.16 (m, 1H), 7.85 (s, 1H), 7.68 (d, 1H), 7.34 (t, 1H), 7.05 (d, 1H), 5.72 (m, 1H), 4.36 (t, 1H), 1.73 (d, 3H), 1.63 (m, 2H), 0.95 (m, 3H) |
| 47 | A | 519.30 | 1.80 | DMSO-$d_6$ (300 MHz): 10.99 (s, 1H), 10.50 (s, 1H), 9.08 (d, 1H), 8.44 (s, 1H), 8.20 (d, 1H), 7.92 (s, 1H), 7.73 (d, 1H), 7.36 (m, 2H), 7.06 (dd, 1H), 5.74 (m, 1H), 4.31 (d, 2H), 3.18 (m, 4H), 1.74 (d, 3H), 1.26 (t, 6H) |
| 48 | B | 510.20 | 3.20 | DMSO-$d_6$ (300 MHz): 9.94 (s, 1H), 9.14 (d, 1H), 8.44 (s, 1H), 7.87 (s, 1H), 7.69 (d, 1H), 7.50 (m, 6H), 7.33 (t, 1H), 7.03 (m, 2H), 5.77 (m, 1H), 1.76 (d, 3H) |
| 49 | B | 516.20 | 3.60 | DMSO-$d_6$ (300 MHz): 10.06 (s, 1H), 9.03 (d, 1H), 8.24 (s, 1H), 8.13 (d, 1H), 7.88 (s, 1H), 7.70 (d, 1H), 7.33 (t, 1H), 7.06 (m, 2H), 5.72 (m, 1H), 2.41 (d, 2H), 1.75 (d, 3H), 1.6-1.1 (m, 9H) |
| 50 | B | 476.20 | 3.10 | DMSO-$d_6$ (300 MHz): 9.94 (s, 1H), 9.04 (d, 1H), 8.25 (d, 1H), 8.15 (m, 1H), 7.86 (t, 1H), 7.68 (dd, 1H), 7.34 (t, 1H), 7.05 (d, 1H), 5.72 (m, 1H), 2.36 (t, 2H), 1.73 (d, 3H), 1.51 (m, 2H), 0.96 (t, 3H) |
| 51 | B | 490.20 | 3.30 | DMSO-$d_6$ (300 MHz): 9.96 (s, 1H), 9.02 (d, 1H), 8.22 (s, 1H), 8.15 (m, 1H), 7.85 (t, 1H), 7.68 (dd, 1H), 7.34 (t, 1H), 7.05 (m, 2H), 5.72 (m, 1H), 1.74 (d, 3H), 1.24 (s, 9H) |
| 52 | B | 438.20 | 2.70 | DMSO-$d_6$ (300 MHz): 9.98 (s, 1H), 9.06 (d, 1H), 8.15 (d, 1H), 8.13 (s, 1H), 7.95 (s, 1H), 7.65 (d, 1H), 7.35 (t, 1H), 7.06 (d, 2H), 5.77 (m, 1H), 2.50 (covered by DMSO, 2H), 1.75 (d, 3H), 1.05 (t, 3H) |
| 53 | B | 511.20 | 2.60 | DMSO-$d_6$ (300 MHz): 9.94 (s, 1H), 9.20 (d, 1H), 8.62 (m, 1H), 8.48 (s, 1H), 8.13 (m, 1H), 7.85 (m, 2H), 7.68 (d, 1H), 7.58 (m, 1H), 7.43 (d, 1H), 7.33 (t, 1H), 7.04 (m, 2H), 5.75 (m, 1H), 1.57 (d, 3H) |
| 54 | A | 504.20 | 2.20 | DMSO-$d_6$ (300 MHz): 10.63 (s, 1H), 9.12 (d, 1H), 8.36 (s, 1H), 8.22 (d, 1H), 7.93 (s, 1H), 7.67 (dd, 1H), 7.42 (d, 1H), 7.25 (t, 1H), 6.99 (dd, 1H), 5.73 (m, 1H), 2.39 (s, 3H), 2.29 (s, 3H), 1.75 (d, 3H) |
| 55 | A | 569.30 | 1.90 | DMSO-$d_6$ (300 MHz): 11.16 (br, 1H), 10.70 (s, 1H), 9.41 (d, 1H), 8.87 (s, 1H), 8.23 (d, 1H), 8.08 (d, 2H), 7.96 (s, 1H), 7.75 (m, 2H), 7.63 (m, 2H), 7.45 (d, 1H), 7.25 (d, 1H), 7.01 (dd, 1H), 5.82 (m, 1H), 4.34 (d, 2H), 3.31 (br, 2H), 3.03 (br, 2H), 1.93 (m, 4H), 1.82 (d, 3H) |

TABLE 2-continued

| Compound No. | c-Met Ki (μM) | ESMS (M + H) | HPLC R_t (min.) | ¹H NMR (500 MHz) NMR peaks given as δ values |
|---|---|---|---|---|
| 56 | B | 511.20 | 2.60 | |
| 57 | B | 511.20 | 2.20 | |
| 58 | A | 543.30 | 2.50 | DMSO-d₆ (300 MHz): 9.94 (br, 2H), 9.17 (d, 1H), 8.67 (s, 1H), 8.14 (d, 1H), 7.93 (s, 1H), 7.76 (d, 1H), 7.64 (m, 3H), 7.27 (m, 2H), 7.07 (d, 1H), 6.95 (d, 1H), 5.82 (m, 1H), 2.05 (s, 3H), 1.76 (d, 3H) |
| 59 | B | 487.10 | 1.90 | DMSO-d₆ (300 MHz): 10.42 (s, 1H), 9.59 (s, 2H), 9.17 (d, 1H), 9.05 (s, 1H), 8.79 (d, 1H), 8.20 (d, 1H), 8.03 (dd, 1H), 7.84 (s, 1H), 7.74 (d, 1H), 7.32 (d, 1H), 7.25 (t, 1H), 6.97 (d, 1H), 5.92 (m, 1H), 1.83 (d, 3H) |
| 60 | B | 516.20 | 3.10 | DMSO-d₆ (300 MHz): 9.97 (s, 1H), 9.16 (br, 1H), 8.41 (s, 1H), 8.28 (br, 1H), 7.85 (m, 2H), 7.66 (m, 2H), 7.33 (t, 1H), 7.22 (d, 1H), 7.04 (m, 2H), 5.77 (m, 1H), 1.75 (d, 3H) |
| 61 | B | 474.20 | 3.00 | DMSO-d₆ (300 MHz): 9.95 (s, 1H), 9.06 (d, 1H), 8.23 (s, 1H), 8.13 (d, 1H), 7.85 (s, 1H), 7.68 (dd, 1H), 7.34 (t, 1H), 7.07 (m, 2H), 5.72 (m, 1H), 1.73 (d, 3H), 1.53 (m, 1H), 0.86 (m, 2H), 0.70 (m, 2H) |
| 62 | A | 559.30 | 1.80 | DMSO-d₆ (300 MHz): 10.68 (d, 1H), 9.27 (d, 1H), 9.20 (br, 1H), 8.91 (br, 1H), 8.60 (s, 1H), 8.25 (s, 1H), 8.22 (s, 1H), 8.09 (s, 1H), 7.93 (t, 1H), 7.77 (d, 1H), 7.46 (dd, 1H), 7.28 (t, 1H), 7.00 (d, 1H), 5.82 (m, 1H), 4.46 (m, 1H), 3.38 (dbr, 2H), 3.11 (m, 2H), 2.17 (br, 4H), 1.80 (d, 3H) |
| 63 | B | 495.00 | 1.70 | DMSO-d₆ (300 MHz): d 10.9 (s, 1H), 9.01 (d, 1H), 8.32 (d, 1H), 8.15 (d, 1H), 7.91 (s, 1H), 7.54, (s, 1H), 7.42 (d, 1H), 7.38 (d, 1H), 7.32-7.1 (m, 4H), 7.05 (d, 1H), 5.69 (m, 1H) 3.81 (s, 3H), 1.7 (d, 3H). |
| 64 | B | 395.20 | 2.71 | DMSO-d₆ (300 MHz): 9.26 (d, 1H), 8.88 (s, 1H), 8.48 (d, 1H), 8.13 (d, 2H), 7.95-7.36 (m, 6H)5.87-5.76 (m, 1H), 1.77 (d, 3H) |
| 65 | A | 515.20 | 1.80 | DMSO-d₆ (300 MHz): 10.24 (s, 1H), 9.34 (d, 1H), 8.87 (s, 1H), 8.31 (br, 3H), 8.17 (d, 1H), 8.11 (d, 2H), 7.88 (s, 1H), 7.73 (d, 1H), 7.50 (d, 2H), 7.29 (t, 1H), 7.20 (d, 1H), 7.00 (d, 1H), 5.82 (m, 1H), 4.18 (m, 2H), 1.81 (d, 3H) |
| 66 | A | 585.30 | 1.80 | DMSO-d₆ (300 MHz): 9.97 (s, 1H), 9.30 (d, 1H), 8.89 (s, 1H), 8.17 (d, 1H), 8.14 (d, 2H), 7.86 (s, 1H), 7.70 (d, 1H), 7.55 (d, 2H), 7.31 (t, 1H), 7.04 (m, 2H), 5.83 (m, 1H), 4.37 (m, 3H), 3.52 (m, 2H), 3.18 (m, 2H), 2.25 (m, 1H), 2.00 (m, 1H), 1.81 (d, 3H) |
| 67 | A | 585.30 | 1.80 | DMSO-d₆ (300 MHz): 9.96 (s, 1H), 9.29 (d, 1H), 8.88 (s, 1H), 8.17 (d, 1H), 8.14 (d, 2H), 7.86 (s, 1H), 7.70 (d, 1H), 7.55 (d, 2H), 7.31 (t, 1H), 7.04 (m, 2H), 5.83 (m, 1H), 4.38 (m, 3H), 3.52 (m, 2H), 3.16 (m, 2H), 2.25 (m, 1H), 2.00 (m, 1H), 1.81 (d, 3H) |
| 68 | A | 585.30 | 1.80 | DMSO-d₆ (300 MHz): 10.72 (s, 1H), 9.33 (d, 1H), 9.01 (br, 2H), 8.83 (s, 1H), 8.25 (d, 1H), 7.98 (m, 2H), 7.79 (d, 1H), 7.59 9d, 1H), 7.46 (m, 4H), 7.29 (t, 1H), 7.02 (d, 1H), 5.85 (m, 1H), 3.21 (br, 4H), 2.27 (br, 2H), 1.83 (d, 3H), 1.77 (br, 2H) |
| 69 | A | 570.30 | 1.90 | DMSO-d₆ (300 MHz): 11.12 (s, 1H), 9.76 (sbr, 2H), 9.40 (d, 1H), 8.87 (s, 1H), 8.20 (d, 1H), 8.00 (s, 1H), 7.83 (d, 1H), 7.57 (m, 3H), 7.24 (dd, 2H), 6.97 (m, 2H), 5.77 (m, 1H), 3.49 (sbr, 4H), 3.20 (sbr, 4H), 1.80 (d, 3H) |

TABLE 2-continued

| Compound No. | c-Met Ki (μM) | ESMS (M + H) | HPLC R$_t$ (min.) | $^1$H NMR (500 MHz) NMR peaks given as δ values |
|---|---|---|---|---|
| 70 | A | 587.30 | 1.90 | DMSO-d$_6$ (300 MHz): .826 (br, 1H), 10.41 (s, 1H), 9.46 (d, 1H), 8.91 (s, 1H), 8.20 (d, 1H), 8.07 (d, 1H), 7.96 (d, 1H), 7.85 (s, 1H), 7.74 (m, 2H), 7.30 (d, 1H), 7.23 (t, 1H), 6.95 (dd, 1H), 5.82 (m, 1H), 4.41 (d, 2H), 3.42 (br, 2H), 3.09 (br, 2H), 1.94 (m, 4H), 1.82 (d, 3H) |
| 71 | B | 488.30 | 1.70 | DMSO-d$_6$ (300 MHz): 9.26 (d, 1H), 8.90 (s, 1H), 8.23 (d, 1H), 8.17 (d, 2H), 7.61 (mbr, 4H), 7.01 (d, 1H), 5.81 (m, 1H), 4.28 (m, 4H), 3.06 (br, 4H), 1.91 (br, 4H), 1.80 (d, 3H), 1.21 (t, 3H) |
| 72 | A | 570.30 | 1.80 | DMSO-d$_6$ (300 MHz): 10.82 (s, 1H), 9.39 (sbr, 2H), 9.28 (d, 1H), 8.77 (s, 1H), 8.22 (d, 1H), 7.97 (s, 1H), 7.91 (d, 2H), 7.82 (d, 1H), 7.48 (d, 1H), 7.31 (t, 1H), 7.02 (d, 1H), 6.94 (d, 2H), 5.85 (m, 1H), 3.44 (sbr, 4H), 3.21 (sbr, 4H), 1.82 (d, 3H) |
| 73 | A | 565.40 | 1.80 | |
| 74 | B | 382.30 | 2.30 | |
| 75 | B | 381.30 | 2.60 | |
| 76 | A | 543.30 | 1.80 | DMSO-d$_6$ (300 MHz): 10.35 (br, 1H), 9.38 (d, 1H), 8.88 (s, 1H), 8.19 (d, 1H), 8.12 (d, 2H), 7.89 (s, 1H), 7.74 (m, 1H), 7.57 (d, 2H), 7.26 (t, 1H), 6.99 (d, 1H), 5.83 (m, 1H), 4.28 (d, 2H), 2.70 (s, 6H), 1.82 (d, 3H) |
| 77 | A | 569.30 | 2.00 | DMSO-d$_6$ (300 MHz): 10.50 (br, 1H), 9.41 (d, 1H), 8.84 (s, 1H), 8.22 (d, 1H), 7.91 (m, 3H), 7.71 (m, 2H), 7.31 (m, 5H), 6.99 (d, 1H), 5.74 (m, 1H), 3.75 (m, 1H, covered by water), 3.41 (br, 2H), 2.98 (br, 2H), 1.95 (br, 4H), 1.77 (d, 3H) |
| 78 | A | 529.20 | 1.90 | DMSO-d$_6$ (300 MHz): 10.56 (s, 1H), 9.38 (d, 1H), 9.31 (br, 2H), 8.86 (s, 1H), 8.20 (d, 1H), 8.08 (d, 2H), 7.91 (s, 1H), 7.74 (d, 1H), 7.55 (d, 2H), 7.37 (d, 1H), 7.26 (t, 1H), 6.98 (d, 1H), 5.82 (m, 1H), 4.12 (s, 2H), 3.65 (3H covered by water), 1.82 (d, 3H) |
| 79 | B | 458.30 | 1.60 | DMSO-d$_6$ (300 MHz): 11.10 (brs, 1H), 9.30 (d, 1H), 8.92 (s, 1H), 8.27 (d, 1H), 8.20 (d, 2H), 7.72 (d, 2H), 7.32 (d, 1H), 5.85 (m, 1H), 4.38 (d, 2H), 3.35 (br, 2H), 3.06 (br, 2H), 2.57 (s, 3H), 1.97 (m, 4H), 1.75 (d, 3H) |
| 80 | A | 520.30 | 1.80 | DMSO-d$_6$ (300 MHz): 11.20 (brs, 1H), 9.38 (d, 1H), 8.90 (s, 1H), 8.45 (d, 1H), 8.18 (d, 2H), 8.07 (d, 2H), 8.01 (d, 1H), 7.66 (d, 2H), 7.46 (m, 3H), 5.99 (m, 1H), 4.34 (d, 2H), 3.32 (br, 2H), 3.03 (br, 2H), 2.01 (m, 4H), 1.88 (d, 3H) |
| 81 | B | 443.20 | 2.90 | DMSO-d$_6$ (300 MHz): 9.04 (d, 1H), 8.76 (s, 1H), 8.47 (d, 1H), 8.11 (m, 2H), 8.01 (d, 1H), 7.72 (dd, 1H), 7.56 (m, 3H), 7.45 (dd, 1H), 7.09 (dd, 1H), 5.96 (m, 1H), 1.85 (d, 3H) |
| 82 | B | 441.30 | 2.30 | DMSO-d$_6$ (300 MHz): 9.25 (d, 1H), 8.57 (s, 1H), 8.46 (d, 1H), 8.30 (s, 1H), 8.08 (m, 3H), 8.02 (d, 1H), 7.51 (m, 3H), 5.98 (m, 1H), 3.84 (s, 3H), 1.87 (d, 3H) |
| 83 | A | 510.30 | 1.70 | DMSO-d$_6$ (300 MHz): 9.24 (d, 1H), 9.18 (br, 1H), 8.90 (br, 1H), 8.62 (s, 1H), 8.46 (d, 1H), 8.38 (s, 1H), 8.17 (s, 1H), 8.08 (d, 2H), 8.01 (d, 1H), 7.52 (m, 3H), 5.96 (m, 1H), 4.37 (1H, covered by water), 3.37 (br, 2H), 3.04 (br, 2H), 2.17 (br, 4H), 1.86 (d, 3H) |

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

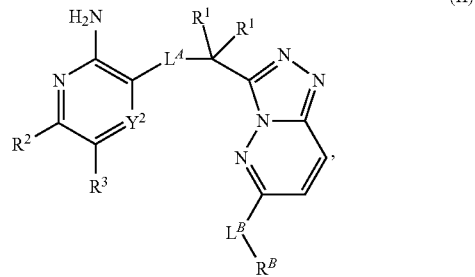

(II)

$Y^2$ is N or CH; or a pharmaceutically acceptable salt or prodrug thereof, wherein:
  $L^A$ is —C(O)NR$^4$—;
  each R$^1$ is, independently, hydrogen or $C_{1-4}$ aliphatic, optionally substituted with substituents independently selected from halogen, —OH, —OR$^5$, —SR$^5$, —NO$_2$, —CN, or —N(R$^5$)$_2$, or two R$^1$ groups bonded to the same carbon form a 3-5 membered carbocyclic ring;
  R$^2$ is hydrogen, halogen, or $C_{1-4}$ aliphatic, or R$^2$ and R$^3$, together with the carbons to which they are bonded, form a 6-membered aryl or 5-6 membered heteroaryl ring, wherein each ring is optionally substituted with up to two R$^{Ar1}$;
  R$^3$ is a $C_{1-8}$ aliphatic or $C_3$-$C_8$ cycloaliphatic group, optionally substituted with R; a 6 or 10 membered aryl; a 5-10 membered heteroaryl having 1-4 heteroatoms independently selected from nitrogen, oxygen, and sulfur; or a 3-10 membered heterocyclyl having 1-4 heteroatoms independently selected from nitrogen, oxygen, and sulfur; wherein each of said aryl, heteroaryl, or heterocyclyl is optionally substituted with one to five R$^{Ar1}$, or R$^3$ and R$^2$, together form a 6-membered aryl or 5-6 membered heteroaryl ring, wherein each ring is optionally substituted with up to two R$^{Ar1}$;
  each R$^4$ is, independently, hydrogen or a $C_{1-4}$ aliphatic, optionally substituted with 1-5 groups independently selected from halogen, $C_{1-4}$ aliphatic, halo($C_{1-4}$ aliphatic), OR$^5$, O(halo($C_{1-4}$ aliphatic)), NO$_2$, CN, CO$_2$R$^5$, C(O)N(R$^5$)$_2$, or N(R$^5$)$_2$;
  $L^B$ is a covalent bond between R$^B$ and the carbon to which $L^B$ is bonded, or is a divalent $C_{1-4}$ alkyl chain which is optionally substituted with 1-5 groups independently selected from halogen, $C_{1-4}$ aliphatic, halo($C_{1-4}$ aliphatic), OR$^5$, O(halo($C_{1-4}$ aliphatic)), NO$_2$, CN, CO$_2$R$^5$, C(O)N(R$^5$)$_2$, or N(R$^5$)$_2$, wherein up to two saturated carbons of said alkylidene chain are replaced by —C(O)—, —C(O)N(R$^5$)—, —C(O)N(R$^5$)N(R$^5$)—, —CO$_2$—, —N(R$^5$)—, —N(R$^5$)C(O)—, —N(R$^5$)CO$_2$—, —N(R$^5$)S(O)$_2$—, —N(R$^5$)C(O)N(R$^5$)—, —N(R$^5$)N(R$^5$)—, —O—, —OC(O)—, —OC(O)N(R$^5$)—, —S—, —SO—, —S(O)$_2$—, or —S(O)$_2$N(R$^5$)—;
  R$^B$ is hydrogen, a $C_{1-8}$ aliphatic, a $C_3$-$C_8$ cycloaliphatic group, optionally substituted with R; a 6 or 10 membered aryl ring; a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with one to five R$^{Ar2}$;
  R is halogen, —R$^6$, —OR$^6$, —SR$^6$, —OC(O)($C_{1-8}$ aliphatic), Ph optionally substituted with R$^6$, —O(Ph) optionally substituted with R$^6$, —CH$_2$(Ph) optionally substituted with R$^6$, —CH$_2$CH$_2$(Ph) optionally substituted with R$^6$, —NO$_2$, —CN, —N(R$^6$)$_2$, —NR$^6$C(O)R$^6$, —NR$^6$C(O)N(R$^6$)$_2$, —NR$^6$CO$_2$R$^6$, —NR$^6$NR$^6$C(O)R$^6$, —NR$^6$NR$^6$C(O)N(R$^6$)$_2$, —NR$^6$NR$^6$CO$_2$R$^6$, —C(O)C(O)R$^6$, —C(O)CH$_2$C(O)R$^6$, —CO$_2$R$^6$, —C(O)R$^6$, —C(O)N(R$^6$)$_2$, —OC(O)N(R$^6$)$_2$, —S(O)$_2$R$^6$, —SO$_2$N(R$^6$)$_2$, —S(O)R$^6$, —NR$^6$SO$_2$N(R$^6$)$_2$, —NR$^6$SO$_2$R$^6$, —C(=S)N(R$^6$)$_2$, —C(=NH)—N(R$^6$)$_2$, or —(CH$_2$)$_y$NHC(O)R$^6$, wherein y is 1 to 4; or two R together on the same carbon atom are =O, =S, =NNHR$^7$, =NN(R$^7$)$_2$, =NNHC(O)R$^7$, =NNHCO$_2$($C_{1-8}$ aliphatic), =NNHSO$_2$($C_{1-8}$ aliphatic), or =NR$^7$;
  each R$^{Ar1}$ or R$^{Ar2}$ is, independently, selected from halogen, —R$^6$, —OR$^6$, —SR$^6$, Ph optionally substituted with one to five R$^6$, —O(Ph) optionally substituted with one or more R$^6$, —(CH$_2$)$_y$(Ph) optionally substituted with one to five R$^6$, —NO$_2$, —CN, —N(R$^6$)$_2$, —NR$^6$C(O)R$^6$, —NR$^6$C(O)N(R$^6$)$_2$, —NR$^6$CO$_2$R$^6$, —NR$^6$NR$^6$C(O)R$^6$, —NR$^6$NR$^6$C(O)N(R$^6$)$_2$, —NR$^6$NR$^6$CO$_2$R$^6$, —C(O)CH$_2$C(O)R$^6$, —CO$_2$R$^6$, —C(O)R$^6$, —C(O)N(R$^6$)$_2$, —OC(O)N(R$^6$)$_2$, —S(O)$_2$R$^6$, —SO$_2$N(R$^6$)$_2$, —S(O)R$^6$, —NR$^6$SO$_2$N(R$^6$)$_2$, —NR$^6$SO$_2$R$^6$, —C(S)N(R$^6$)$_2$, —C(NH)N(R$^6$)$_2$, and —(CH$_2$)$_y$NHC(O)R$^6$, wherein y is 1 to 4; or two adjacent R$^{Ar1}$ or R$^{Ar2}$ together are 1,2-methylenedioxy or 1,2-ethylenedioxy;
  each R$^5$ is, independently, hydrogen or $C_{1-4}$ aliphatic;
  each R$^7$ is, independently, hydrogen or an optionally substituted $C_{1-8}$ aliphatic, wherein each substituent of said optionally substituted aliphatic of R$^7$ is, independently, —NH$_2$, —NH($C_{1-4}$ aliphatic), —N($C_{1-4}$ aliphatic)$_2$, halogen, $C_{1-4}$ aliphatic, —OH, —O($C_{1-4}$ aliphatic), —NO$_2$, —CN, —CO$_2$H, —CO$_2$($C_{1-4}$ aliphatic), —C(O)NH$_2$, —C(O)NH($C_{1-4}$ aliphatic), —C(O)N($C_{1-4}$ aliphatic)$_2$, —O(halo($C_{1-4}$ aliphatic)), or halo($C_{1-4}$ aliphatic); or two R$^7$ on the same nitrogen are taken together with the nitrogen to form a 5-8 membered heterocyclyl or heteroaryl ring having 1-3 heteroatoms independently selected from nitrogen, oxygen, and sulfur; and
  each R$^6$ is, independently, hydrogen, optionally substituted $C_{1-6}$ aliphatic, an unsubstituted 5-6 membered heteroaryl or heterocyclic ring, -Ph, or —O(Ph), wherein each substituent of said optionally substituted aliphatic of R$^6$ is, independently, —NH$_2$, —NH($C_{1-4}$ aliphatic), —N($C_{1-4}$ aliphatic)$_2$, halogen, $C_{1-4}$ aliphatic, —OH, —O($C_{1-4}$ aliphatic), —NO$_2$, —CN, —CO$_2$H, —CO$_2$($C_{1-4}$ aliphatic), —C(O)NH$_2$, —C(O)NH($C_{1-4}$ aliphatic), —C(O)N($C_{1-4}$ aliphatic)$_2$, —O(halo($C_{1-4}$ aliphatic)), or halo($C_{1-4}$ aliphatic); or two R$^6$ on the same nitrogen are taken together with the nitrogen to form a 5-8 membered heterocyclyl or heteroaryl ring having 1-3 heteroatoms independently selected from nitrogen, oxygen, and sulfur.

2. The compound according to claim 1, having the formula:

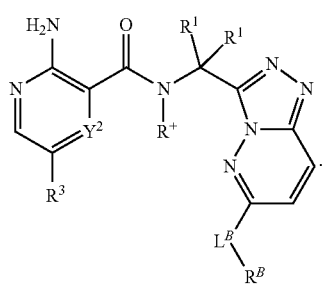
(IIa)

wherein R⁺ is H.

3. The compound according to claim 1, wherein Y² is N.

4. The compound according to claim 1, wherein R³ is an optionally substituted phenyl or 5-6 membered heteroaryl ring.

5. The compound according to claim 4, wherein R³ is an optionally substituted heteroaryl ring selected from furanyl, thienyl, pyrrolyl, pyrazolyl, imidazolyl, oxazolyl, or thiazolyl.

6. The compound according to claim 1, wherein $R^B$ is $C_{1-8}$ aliphatic, a $C_3$-$C_8$ cycloaliphatic group, optionally substituted with R; a 6 or 10 membered aryl ring; a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with one to five $R^{Ar2}$.

7. The compound according to claim 1, wherein $L^B$ is a covalent bond, —CH₂—, or —N(R⁵)—.

8. The compound according to claim 7, wherein $L^B$ is —NH—.

9. The compound according to claim 7, wherein $R^B$ is an optionally substituted phenyl or 5-6 membered heteroaryl ring.

10. The compound according to claim 9, wherein $R^B$ is a phenyl ring substituted in the 3-position.

11. The compound according to claim 9, wherein $R^B$ is an optionally substituted heteroaryl ring selected from furanyl, thienyl, pyrrolyl, pyrazolyl, imidazolyl, oxazolyl, or thiazolyl.

12. A compound selected from the group of compounds consisting of:

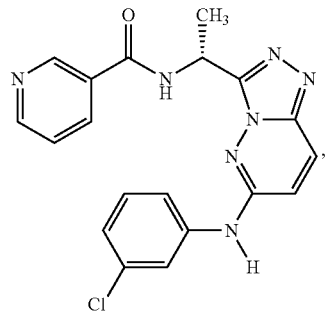

-continued

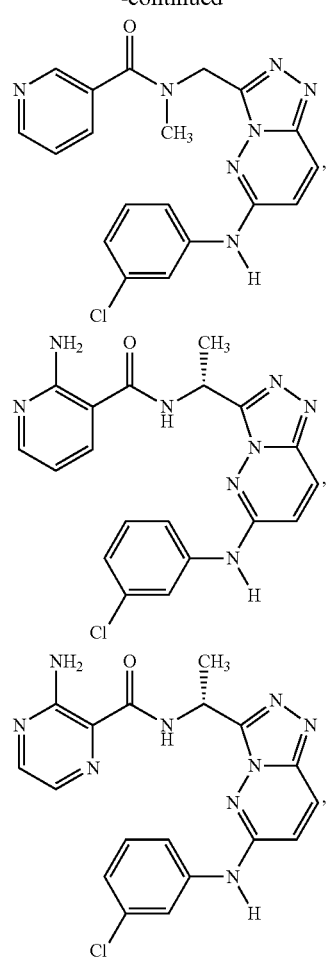

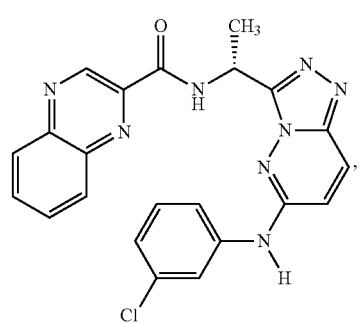

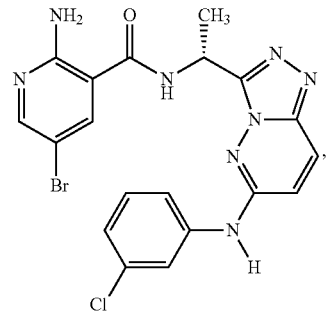

73
-continued
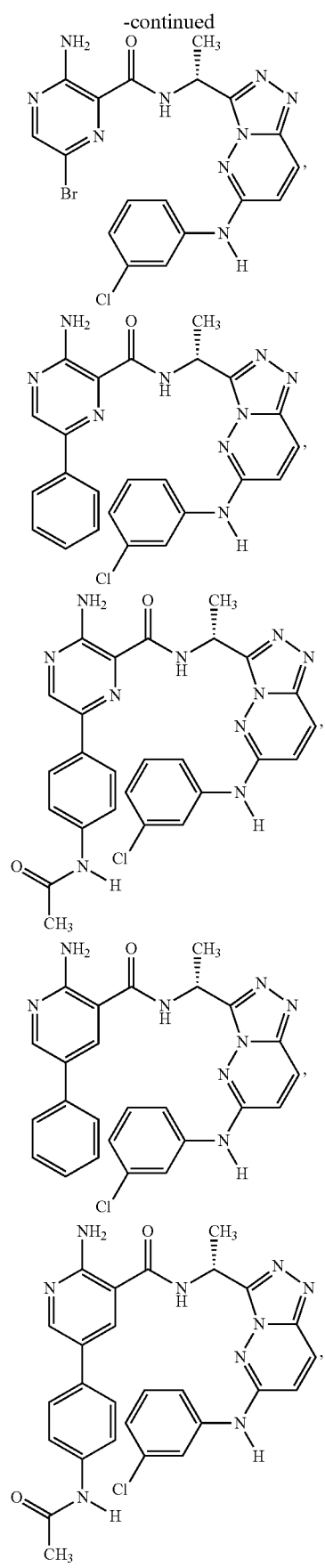
74
-continued
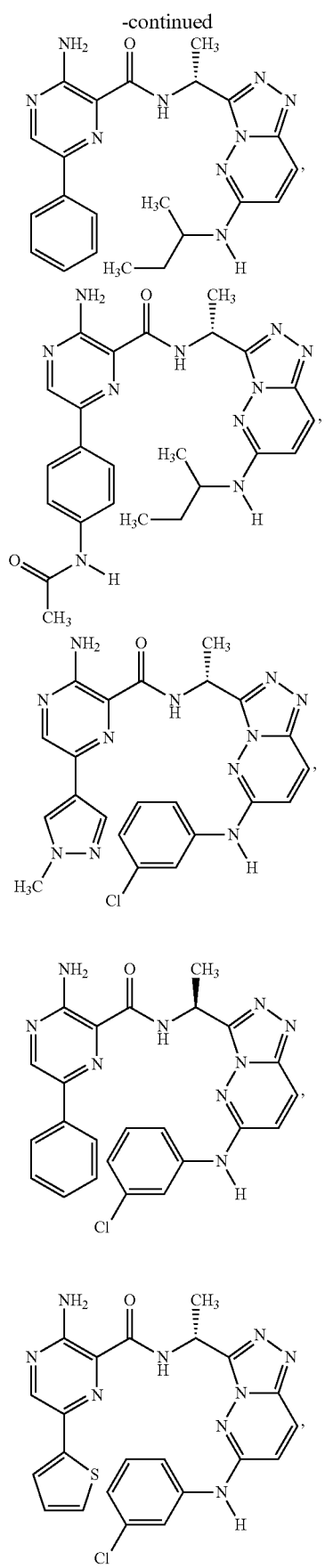

75
-continued
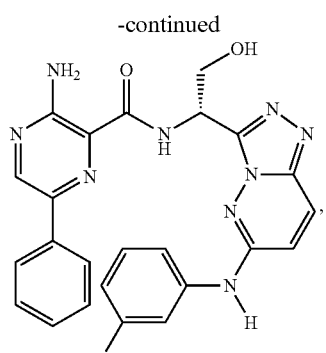
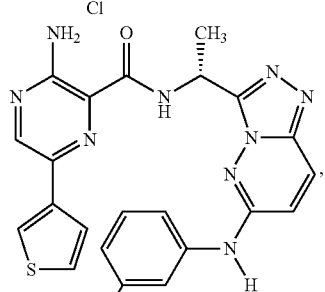
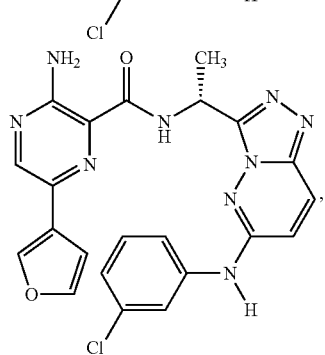
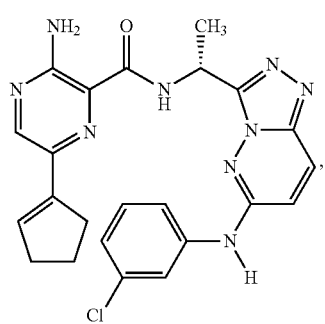
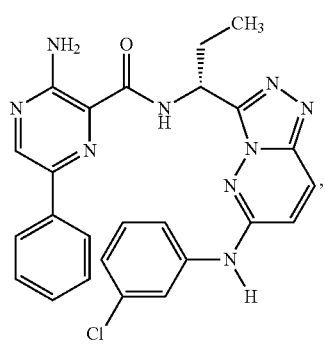
76
-continued
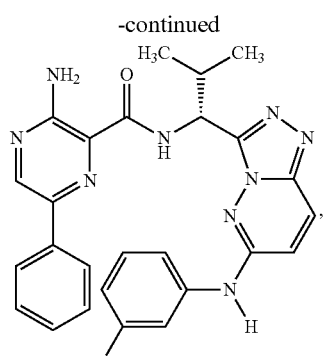
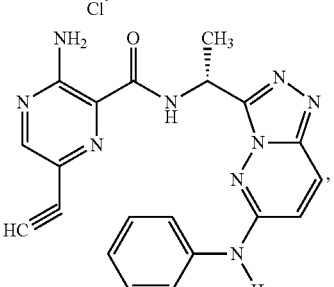
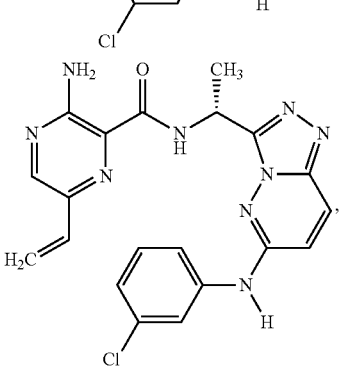
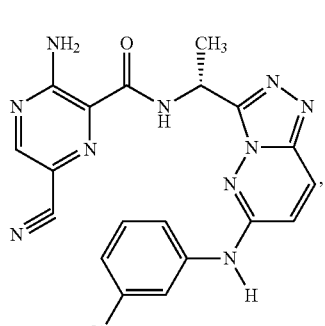
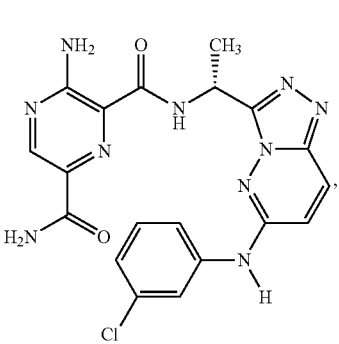

77 -continued

78 -continued

79
-continued
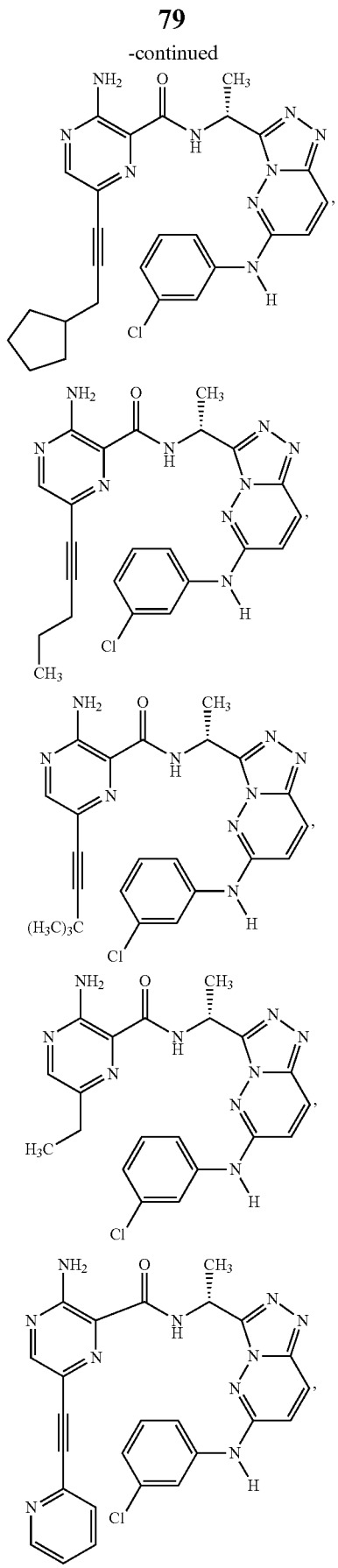
80
-continued
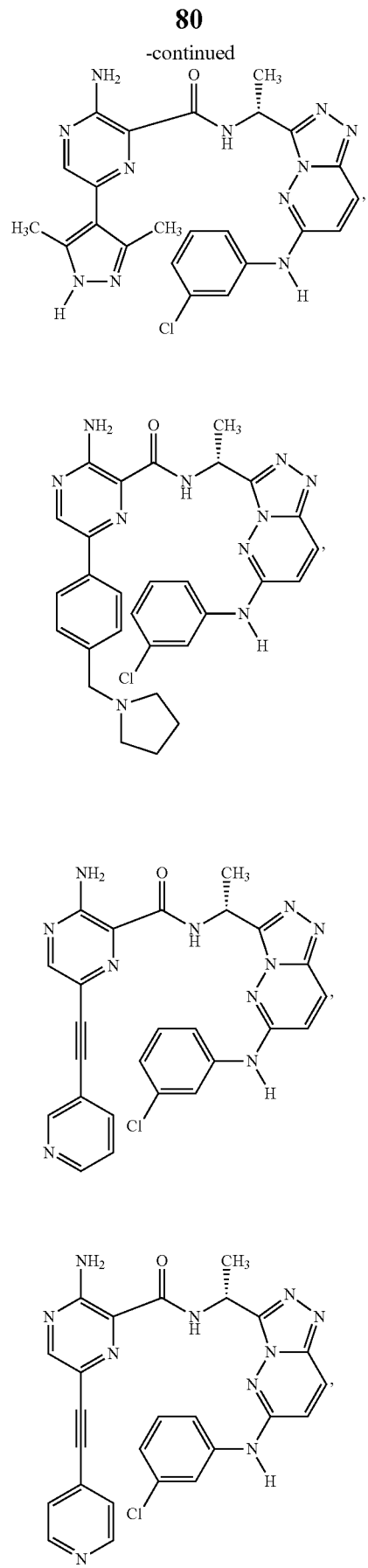

-continued
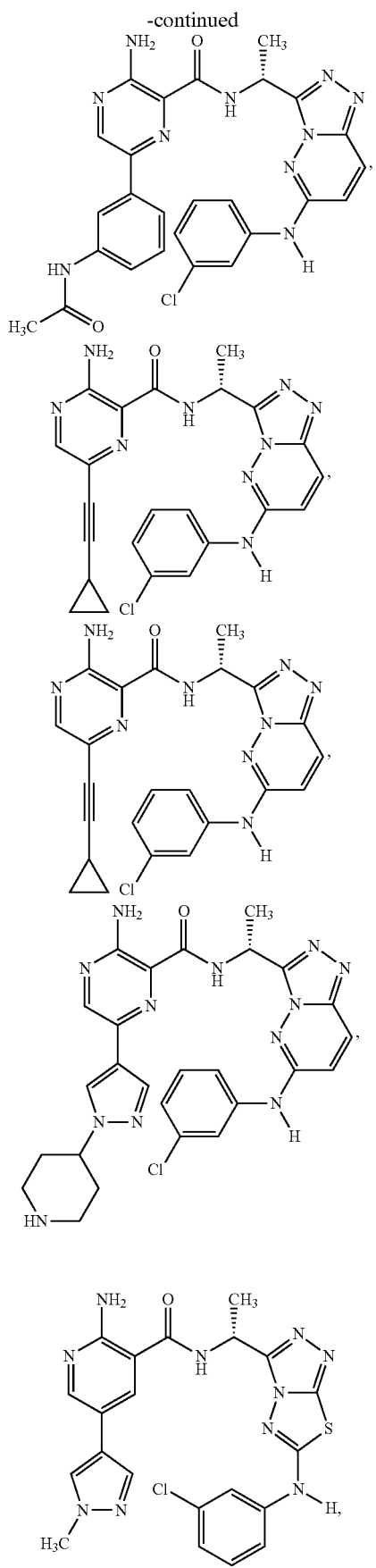
-continued
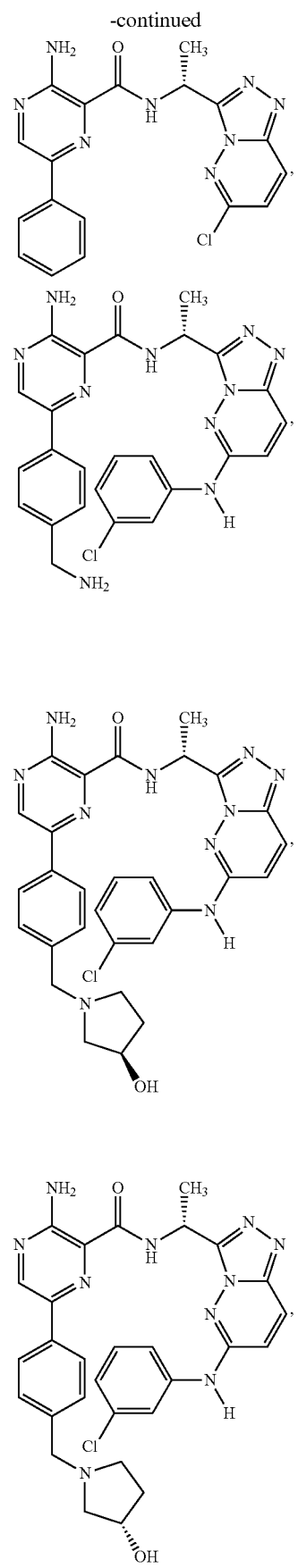

83
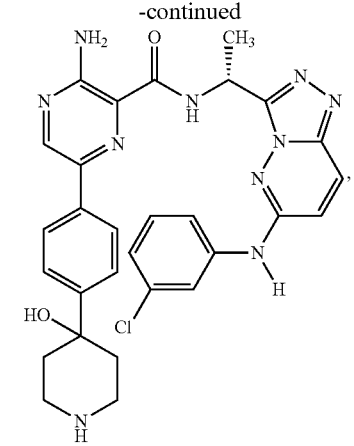
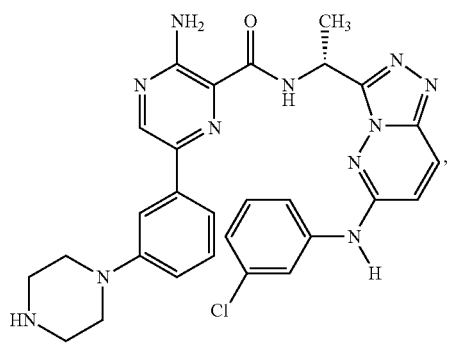
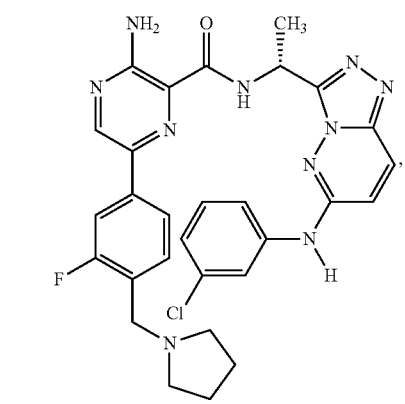
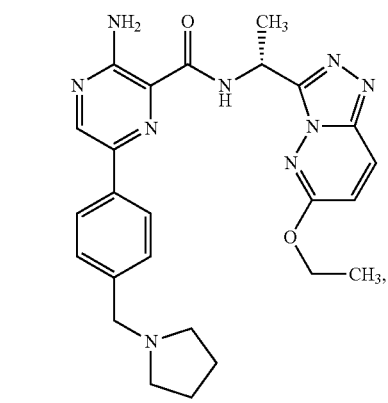
84
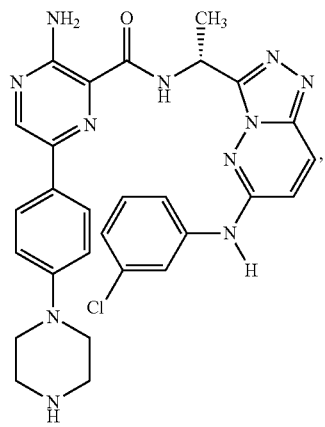
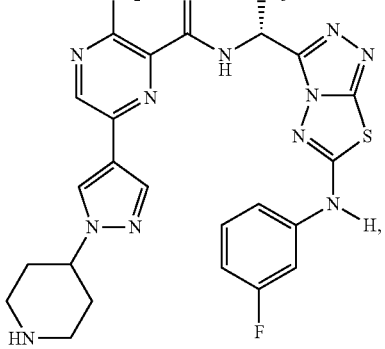
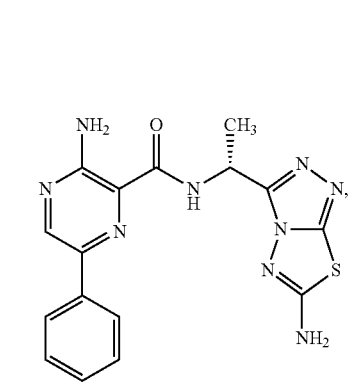
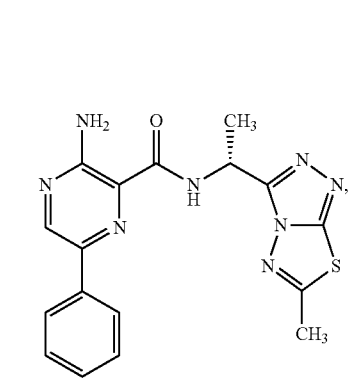

85
-continued
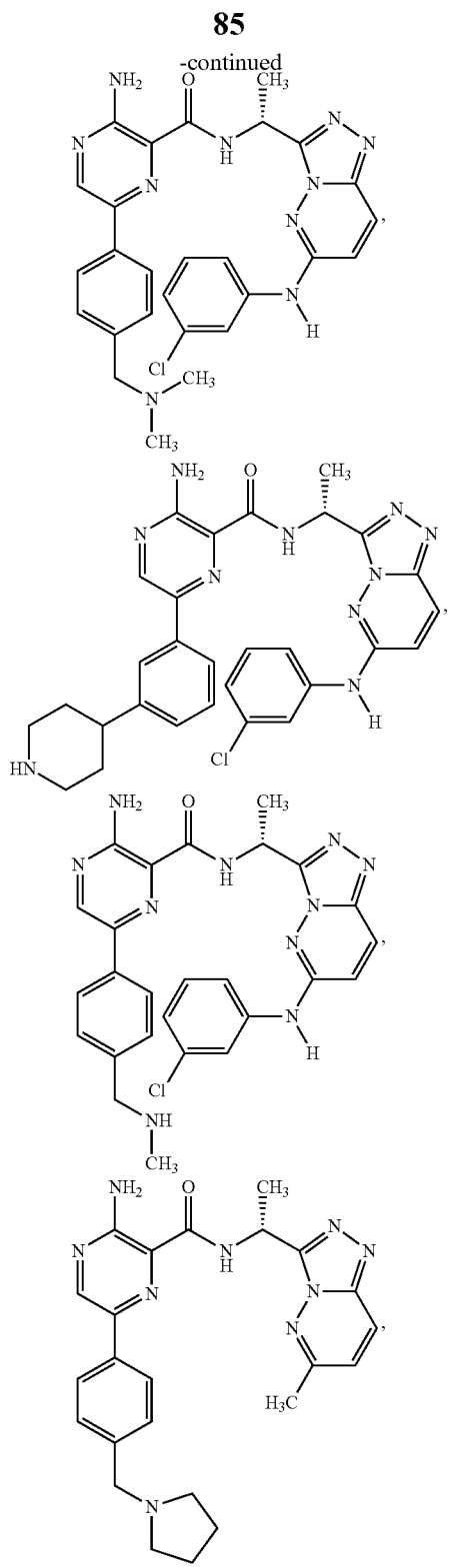
86
-continued
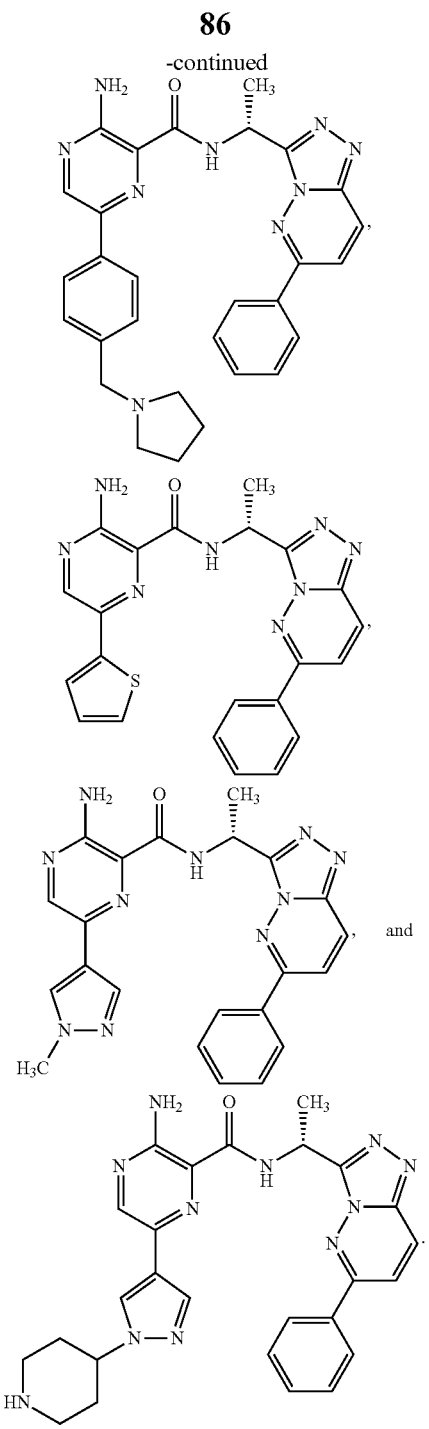
13. A pharmaceutical composition comprising a compound according to claim 1 and a pharmaceutically acceptable carrier, adjuvant, or vehicle.
* * * * *